United States Patent
Lawson et al.

(10) Patent No.: US 10,094,815 B2
(45) Date of Patent: Oct. 9, 2018

(54) METHOD TO ENHANCE EXPLORATION, DEVELOPMENT AND PRODUCTION OF HYDROCARBONS USING MULTIPLY SUBSTITUTED ISOTOPOLOGUE GEOCHEMISTRY, BASIN MODELING AND MOLECULAR KINETICS

(71) Applicants: Michael Lawson, Spring, TX (US); Brian K. Peterson, Fogelsville, PA (US); Cara L. Davis, Houston, TX (US); David R. Converse, Houston, TX (US); John M. Eiler, Sierra Madre, CA (US)

(72) Inventors: Michael Lawson, Spring, TX (US); Brian K. Peterson, Fogelsville, PA (US); Cara L. Davis, Houston, TX (US); David R. Converse, Houston, TX (US); John M. Eiler, Sierra Madre, CA (US)

(73) Assignee: ExxonMobil Upstream Research Company, Spring, TX (US)

( * ) Notice: Subject to any disclaimer, the term of this patent is extended or adjusted under 35 U.S.C. 154(b) by 300 days.

(21) Appl. No.: 14/844,134

(22) Filed: Sep. 3, 2015

(65) Prior Publication Data
US 2016/0084817 A1    Mar. 24, 2016

Related U.S. Application Data

(60) Provisional application No. 62/052,311, filed on Sep. 18, 2014.

(51) Int. Cl.
*G01V 1/40*    (2006.01)
*G01N 33/24*    (2006.01)
(Continued)

(52) U.S. Cl.
CPC .......... *G01N 33/241* (2013.01); *E21B 49/00* (2013.01); *G01V 9/007* (2013.01)

(58) Field of Classification Search
None
See application file for complete search history.

(56) References Cited

U.S. PATENT DOCUMENTS

| 5,388,456 A | 2/1995 | Kettel |
| 6,613,520 B2 | 9/2003 | Ashby |

(Continued)

FOREIGN PATENT DOCUMENTS

| WO | WO 2007/008932 | 1/2007 | |
| WO | WO 2007008932 A2 * | 1/2007 | ......... G01N 21/3504 |

OTHER PUBLICATIONS

Daniel Aaron Stolper: "New Insights into the formation and Modification of Carbonate-Bearing Minerals and Methane Gas in Geological Systems Using Multiply Substituted Isotopologues Thesis", Mar. 13, 2014 (Mar. 13, 2014), XP055229283, Retrieved from internet: URL: http://thesis.library.caltech.edu/8404/1/Stolper_Daniel_2014_Thesis.pdf.*

(Continued)

*Primary Examiner* — Cory Eskridge

(57) ABSTRACT

A method and system are described that may be used for exploration, production and development of hydrocarbons. The method and system may include analyzing a sample for a geochemical signature, wherein the geochemical signature includes a multiply substituted isotopolog signature and/or a position specific isotope signature. Then, the historical temperature, type of alteration and/or extent of alteration may be determined from the signature(s) and used to develop or refine an exploration, development or production strategy.

28 Claims, 7 Drawing Sheets

(51) Int. Cl.
E21B 49/00 (2006.01)
G01V 9/00 (2006.01)

(56) References Cited

U.S. PATENT DOCUMENTS

| | | | |
|---|---|---|---|
| 7,124,030 | B2 | 10/2006 | Ellis |
| 7,174,254 | B2 | 2/2007 | Ellis |
| 7,529,626 | B1 | 5/2009 | Ellis |
| 8,071,295 | B2 | 12/2011 | Ashby |
| 8,316,934 | B2 | 11/2012 | Pietrobon |
| 8,476,016 | B2 | 7/2013 | Ashby |
| 8,505,375 | B2 | 8/2013 | Smalley |
| RE44,728 | E | 1/2014 | Pope et al. |
| 8,760,657 | B2 | 6/2014 | Pope et al. |
| 8,950,251 | B2 | 2/2015 | Valentine |
| 2008/0147326 | A1 | 6/2008 | Ellis |
| 2011/0250582 | A1 | 10/2011 | Gates et al. |
| 2012/0134749 | A1 | 5/2012 | Darrah |
| 2013/0091925 | A1 | 4/2013 | Darrah et al. |
| 2013/0103337 | A1 | 4/2013 | Eiler |
| 2013/0116126 | A1 | 5/2013 | Ashby et al. |
| 2014/0011692 | A1 | 1/2014 | Ashby |
| 2014/0138528 | A1 | 5/2014 | Pope et al. |
| 2014/0162274 | A1 | 6/2014 | Kunin et al. |
| 2015/0038348 | A1 | 2/2015 | Ashby et al. |

OTHER PUBLICATIONS

Ghanbar Hassanzade et al.: "Petroleum Sustem Analysis Using Geochemical Studies, Isotope and 1D Basin Modeling in Hendijan Oil Field, SW Iran", International Petroleum Technology Conference, Feb. 7, 2012 (Feb. 7, 2012), XP055229960, DOI: 10.2523/IPTC-14797-MS.*

Wang, Y., et al., "Thermal cracking history by laboratory kinetic simulation of Paleozoic oil in eastern Tarim Basin, NW China, implications for the occurrence of residual oil reservoirs," *Organic Geochemistry* 65, ScienceDirect, Elsevier, pp. 1803-1815 (2006).

Mudford, B. et al., "Timing of hydrocarbon generation and accumulation in fault-bounded compartments in the Norphlet Formation, offshore Alabama," *Marine and Petroleum Geology* 12(5), pp. 549-558 (1995).

Hassanzadeh, G. et al., "Petroleum System Analysis Using Geochemical Studies, Isotope and 1D Basin Modeling in Hendijan Oil Field, SW Iran," International Petroleum Technology Conf., IPTC 14797, Bangkok, Thailand, 11 pgs. (Feb. 7-9, 2012).

Lee, G.H. et al., "Timing of trap formation in the southwestern margin of the Ulleung Basin, East Sea (Japan Sea) and implications for hydrocarbon accumulations," *Geosciences Journal* 8(4), pp. 369-380 (Dec. 2004).

Stolper, A., "New Insights into the Formation and Modification of Carbonate-Bearing Minerals and Methane Gas in Geological Systems Using Multiply Substituted Isotopologues," Thesis, California Institute of Technology, Part 1, pp. 1-77 (Defended May 13, 2014).

Stolper, A., "New Insights into the Formation and Modification of Carbonate-Bearing Minerals and Methane Gas in Geological Systems Using Multiply Substituted Isotopologues," Thesis, California Institute of Technology, Part 2, pp. 78-161 (Defended May 13, 2014).

Stolper, A., "New Insights into the Formation and Modification of Carbonate-Bearing Minerals and Methane Gas in Geological Systems Using Multiply Substituted Isotopologues," Thesis, California Institute of Technology, Part 3, pp. 162-245 (Defended May 13, 2014).

Stolper, A., "New Insights into the Formation and Modification of Carbonate-Bearing Minerals and Methane Gas in Geological Systems Using Multiply Substituted Isotopologues," Thesis, California Institute of Technology, Part 4, pp. 246-305 (Defended May 13, 2014).

Xiao, X.M. et al., "Tracing of deeply-buried source rock: A case study of the WC9-2 petroleum pool in the Pearl River Mouth Basin, South China Sea," *Marine and Petroleum Geology* 26, pp. 1365-1378 (2009).

Berner, U., et al. (1988), "Maturity Related Mixing Model for Methane, Ethane and Propane, Based on Carbon Isotopes", Advances in Organic Geochemistry, vol. 13, Nos. 1-3, pp. 67-72.

Stahl, W.J., (1977), "Carbon and Nitrogen Isotopes in Hydrocarbon Research and Exploration", Chemical Geology, vol. 20, pp. 121-149.

Chung, H.M., et al., (1979), "Use of Stable Carbon Isotope Compositions of Pyrolytically Derived Methane As Maturity Indices for Carbonaceous Materials", Geochimica et Cosmochimica Acta, vol. 43, pp. 1979-1988.

James, A.T., (1990), "Correlation of Reservoired Gases Using The Carbon Isotopic Compositions of Wet Gas Components", The American Association of Petroleum Geologists Bulletin, vol. 74, No. 9, pp. 1441-1458.

Whiticar, M.J., (1996), "Stable Isotope Geochemistry of Coals, Humic Kerogens and Related Natural Gases", vol. 32, pp. 191-215.

Stolper, D.A., et al. (2014), "Formation Temperatures of Thermogenic and Biogenic Methane", Science, vol. 344, pp. 1500-1503.

Stolper, D.A., et al., (2014), "Combined 13C-D and D-D Clumping in Methane: Methods and Preliminary Results", Geochimica et Cosmochimica Acta, vol. 126, pp. 169-191.

Urey, H.C., et al., (1933), "Some Thermodynamic Properties of the H1H2, H2H2 Molecules and Compounds Containing The H2 Atom", Journal of Chemical Physics, vol. 1, pp. 137-143.

Bigeleisen, J., et al., (1947), "Calculation of Equilbrium Constants for Isotopic Exchange Reactions", The Journal of Chemical Physics, vol. 15, No. 5., pp. 261-267.

Richet, R., et al., (1977), "A Review of Hydrogen, Carbon, Nitrogen, Oxygen, Sulphur, and Chlorine Stable Isotope Fractionation Among Gaseous Molecules", Ann. Rev. Earth Planet Sci., vol. 5, pp. 65-110.

Vidler, M., et al., (2000), "Accurate Partition Function and Thermodynamic Data For Water", Journal of Chemical Physics, vol. 113, No. 21, pp. 9766-9771.

Liu, Q., et al., (2010), "On the Proper Use of The Bigeleisen-Mayer Equation and Corrections to it in the Calculation of Isotopic Fractionation Equilibrium Constants", Geochimica et Cosmochimica Acta, vol. 74, pp. 6965-6983.

Bloino, J., et al., (2012), "General Perturbative Approach for Spectroscopy, Thermodynamics, and Kinetics: Methodological Background and Benchmark Studies", J. Chem. Theory Comput., vol. 8, pp. 1015-1036.

Truhlar, D.G., et al., (1991), "Simple Perturbation Theory Estimates of Equilibrium Constants From Force Fields", J. Chem. Phys., vol. 94 (1), pp. 357-359.

Webb, M.A., et al., (2014), "Position-Specific and Clumped Stable Isotope Studies: Comparison of The Urey and Path-Integral Approaches for Carbon Dioxide, Nitrous Oxide, Methane, and Propane", J. Phys. Chem. A, vol. 118, pp. 467-474.

Rustad, J.R., et al., (2010), "Calculation of Boron-Isotope Fractionation Between B(OH)3(aq) and B(OH)4-(aq)", Geochimica et Cosmochimica Acta, vol. 74, pp. 2843-2850.

Wang, Y., et al., (2009), "Equilibrium 2H/1H Fractionations in Organic Moldecules: I. Experimental Calibration of Ab Initio Calculations", Geochimica et Cosmochimica Acta, vol. 73, pp. 7060-7075.

Reeves, E.P., et al., (2012), "Hydrogen Isotope Exchange Between n-Alkanes and Water Under Hydrothermal Conditions", Geochimica et Cosmochimica Acta, vol. 77, pp. 582-599.

Glasstone, S., et al., (1941), "The Theory of Rate Processes", McGraw-Hill, New York, pp. 249.

Burnham, A.K., et al., (1989), "A Chemical Kinetic Model of Vitrinite Maturation and Reflectance", Geochimica et Cosmochimica Acta, vol. 53, pp. 2649-2657.

Sweeney, J. J., et al., (1990), "Evaluation of a Simple Model of Vitrinite Reflectance Based on Chemical Kinetics", The American Association of Petroleum Geologists Bulletin, vol. 74, No. 10, pp. 1559-1570.

Magoon, L.B., et al., (1994), "The Petroleum System—From Source to Trap", AAPG Memoir 60, pp. 3-24.

(56) References Cited

OTHER PUBLICATIONS

Rustad, J.R., et al., (2007), "Ab Initio Calculation of Isotopic Fractionation in B(OH)3(aq) and BOH4-(aq)", JACS Communications, pp. 2222-2223.

* cited by examiner

METHOD TO ENHANCE EXPLORATION, DEVELOPMENT AND PRODUCTION OF HYDROCARBONS USING MULTIPLY SUBSTITUTED ISOTOPOLOGUE GEOCHEMISTRY, BASIN MODELING AND MOLECULAR KINETICS

CROSS-REFERENCE TO RELATED APPLICATION

This application claims the benefits of U.S. Provisional Patent Application 62/052,311 filed Sep. 18, 2014 entitled METHOD TO ENHANCE EXPLORATION, DEVELOPMENT AND PRODUCTION OF HYDROCARBONS USING MULTIPLY SUBSTITUTED ISOTOPOLOGUE GEOCHEMISTRY, BASIN MODELING AND MOLECULAR KINETICS, the entirety of which is incorporated by reference herein.

FIELD OF THE INVENTION

The present disclosure relates generally to the field of multiply substituted isotopologue and position specific isotope geochemistry. More particularly, the present disclosure relates to systems and methods for constraining the temperatures of hydrocarbon generation, expulsion, migration, storage, preservation and/or alteration and mixing in hydrocarbon systems. Such information may provide more quantitative constraints on relative and absolute timing on these processes to enhance predictions of the regional confluence of these different processes for optimal prospect evaluation of larger volumes or higher quality of hydrocarbons for subsequent ranking and enhance exploration, development and production operations.

BACKGROUND

This section is intended to introduce various aspects of the art, which may be associated with exemplary embodiments of the present disclosure. This discussion is believed to assist in providing a framework to facilitate a better understanding of particular aspects of the present invention. Accordingly, it should be understood that this section should be read in this light, and not necessarily as admissions of prior art.

Hydrocarbons are generated in the subsurface from source rocks rich in organic matter. Following initial deposition, source rocks are buried and subjected to increasing temperature and pressure with increasing burial. Hydrocarbons are generated when the source rocks reach temperatures sufficient for the thermal conversion of organic material to kerogen and then to free liquid and/or gaseous hydrocarbon phases, which is a process called source rock maturation. Upon generation, the hydrocarbons may subsequently be expulsed from the source rock and migrate in the subsurface to reservoir rocks (such as sandstones or limestones) that have sufficient porosity, structure and an adequate seal that make them capable of trapping the hydrocarbon phase(s), allowing hydrocarbons to accumulate. Alternatively, hydrocarbons may migrate to a surface location (e.g., sometimes referred to as a seep). Any hydrocarbons present in the subsurface may be preserved or they may be subjected to different forms of alteration. For example, biodegradation is the process of degradation or consumption of hydrocarbons by micro-organisms. Similarly, hydrocarbons may be thermally altered by exposure to temperatures above their thermal stability. Alternatively, hydrocarbons may be oxidized or consumed in processes, such as thermochemical sulfate reduction.

Conventional practice uses molecular geochemistry analysis of hydrocarbon compounds in oil samples or gas compositional and stable isotope analysis of hydrocarbon compounds in gaseous samples. These techniques are capable of estimating the maturity of the source rock when hydrocarbons were generated, the source facies from which the hydrocarbons were generated (e.g., marine or terrestrial source rocks), and can sometimes be used to differentiate between different potential origins of hydrocarbons (e.g., biogenic as compared to thermogenic) and provide information on alteration. For example, a series of hydrocarbon composition and stable isotope models were developed to estimate thermal maturity and identify alteration in hydrocarbon gases. See e.g., Stahl, W. J., (1977), "Carbon and Nitrogen Isotopes in Hydrocarbon Research and Exploration", *Chemical Geology*, Vol. 20, pp. 121-149; Berner, U., et al. (1988), "Maturity Related Mixing Model for Methane, Ethane and Propane, Based on Carbon Isotopes", *Advances in Organic Geochemistry*, Vol. 13, pp. 67-72; Chung, H. M., et al., (1979), "Use of Stable Carbon Isotope of Pyrolytically Derived Methane as Maturity Indices for Carbonaceous Materials", *Geochimica et Cosmochimica Acta*, Vol. 43, pp. 1979-1988; James, A. T., (1990), "Correlation of reservoired gases using the carbon isotopic compositions of wet gas components", *AAPG Bulletin*, Vol. 74, No. 9, pp. 1441-1458; Whiticar, M. J., (1996), "Stable isotope geochemistry of coals, humic kerogens and related natural gases", *International Journal of Coal Geology* Vol. 32, pp. 191-215.

Yet, conventional techniques have deficiencies. For example, these conventional techniques do not provide accurate quantitative estimates of hydrocarbon generation temperature. Furthermore, the conventional techniques do not provide an evaluation of the time at which hydrocarbons were first expulsed or migrated in the subsurface, the temperatures at which hydrocarbons are stored in the reservoir or when hydrocarbons underwent mixing (e.g., during migration or in reservoir). Similarly, the conventional techniques do not provide quantitative constraints on how much alteration hydrocarbons have experienced (e.g., from either biodegradation or thermal cracking), and do not provide the temperature and/or time at which alteration occurred, or for how long these processes were taking place.

SUMMARY

According to disclosed aspects and methodologies, a method for exploration, production and development of hydrocarbons is described herein. The method includes obtaining a sample comprising hydrocarbons; analyzing the sample for a geochemical signature, wherein the geochemical signature comprises one or more of a multiply substituted isotopologue signature and a position specific isotope signature; determining one or more of historical temperature, type of alteration, and extent of alteration from one or more of the multiply substituted isotopologue signature and position specific isotope signature; and developing or refining an exploration, development or production strategy based on the determined one or more of one of historical temperature, type of alteration, and extent of alteration.

In one or more embodiments, a computer system for exploration, production and development of hydrocarbons is described. The computer system may include a processor; memory in communication with the processor; and a set of instructions stored in memory and accessible by the processor. The set of instructions, when executed by the processor, are configured to: obtain information associated with a hydrocarbon sample; analyze the information for a geochemical signature, wherein the geochemical signature comprises one or more of a multiply substituted isotopologue signature and a position specific isotope signature; determine one or more of historical temperature, type of alteration, and extent of alteration from one or more of the multiply substituted isotopologue signature and position specific isotope signature; and develop or refining an exploration, development or production strategy based on the determined one or more of one of historical temperature, type of alteration, and extent of alteration.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION

Figure 1:
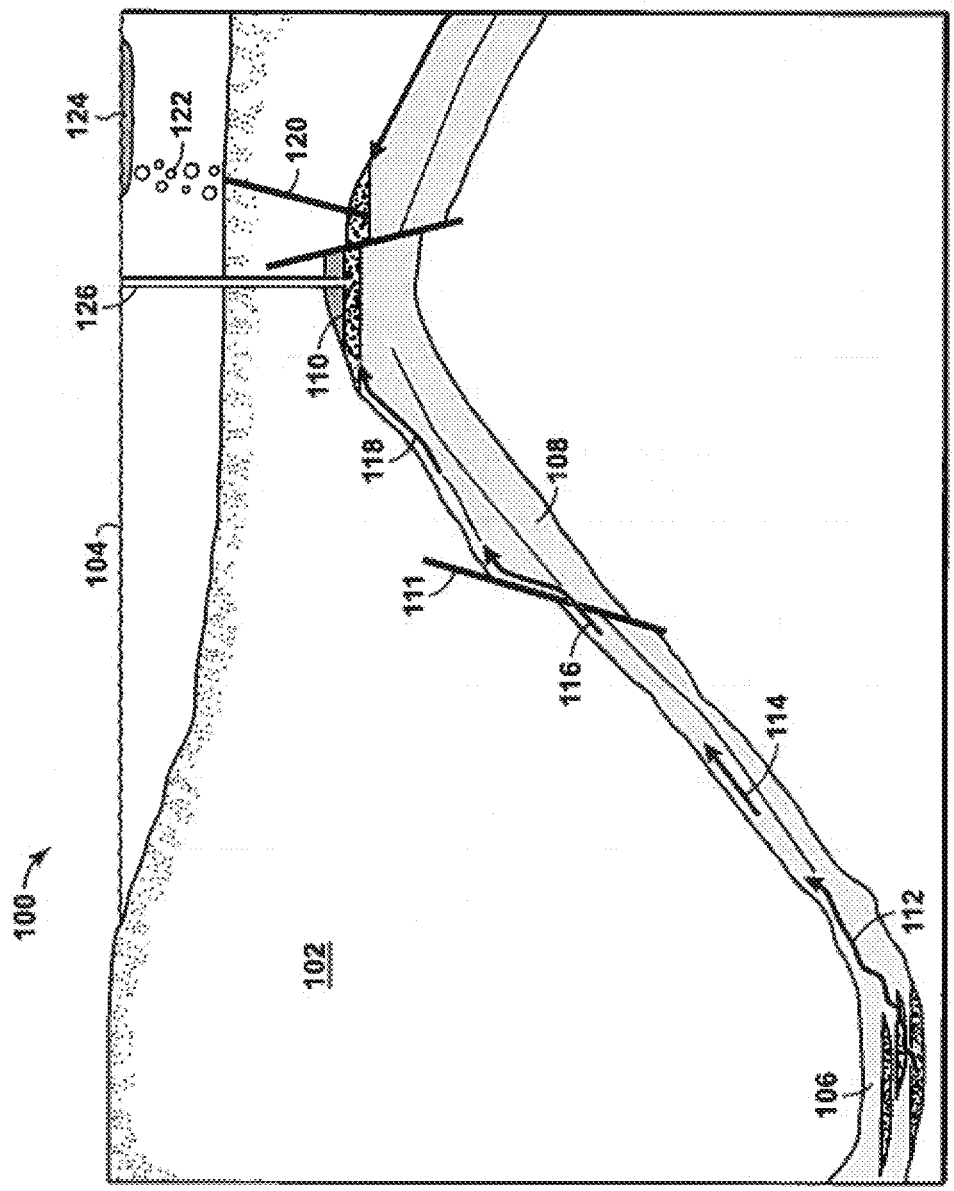
FIG. 1 is a side elevational view of components of a hydrocarbon system in a subsurface region.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, fewer than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

In the following section, specific embodiments of the present techniques are described in connection with disclosed aspects and features. However, to the extent that the following description is specific to a particular aspect, technique, or a particular use, this is intended to be for exemplary purposes only. Accordingly, the invention is not limited to the disclosed aspects and techniques described below, but rather includes all alternatives, modifications, and equivalents falling within the scope of the appended claims.

Various terms as used herein are defined below. To the extent a term used in a claim is not defined below, it should be given the definition persons in the pertinent art have given that term in the context in which it is used.

As used herein, "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprise," "comprised," "containing," "contains," "contain," "having," "has," "have," "including," "includes," and "include" are open-ended transition terms used to transition from a subject recited before the term to one or more elements recited after the term, where the element or elements listed after the transition term are not necessarily the only elements that make up the subject.

As used herein, the term "exemplary" means exclusively "serving as an example, instance, or illustration." Any embodiment described herein as exemplary is not to be construed as preferred or advantageous over other embodiments.

As used herein, the term "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide ($H_2S$) and carbon dioxide ($CO_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicilytes, carbonates, diatomites, and other porous media.

As used herein, "hydrocarbon production" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing the wellbore to promote increased flow, well servicing, well logging, and other well and wellbore treatments.

As used herein, the term "isotope" refers to one of two or more atoms with the same atomic number but with different numbers of neutrons. Hydrocarbon molecules may contain a variety of isotopes. Hydrocarbon molecules contain both carbon and hydrogen atoms. Carbon can be present in the molecule as one of two stable isotopes: $^{12}C$, which has 6 protons and 6 neutrons (shown herein as C); and, in much lower concentrations, $^{13}C$, which has 6 protons and 7 neutrons. Similarly, hydrogen can be present in a molecule as one of two stable isotopes: H, which contains 1 proton but no neutron; and, in much lower concentrations, Deuterium (D), which has 1 proton and 1 neutron.

As used herein the term "historical temperature", refers to any temperature from the point of generation of the hydrocarbon to the temperature at the point of extraction from the reservoir.

As used herein the term "basin modeling", refers generally to any method or analysis, computerized or otherwise, that provides a representation of the history of a sedimentary basin or other subsurface section of interest and/or an estimate of timing of any component of a hydrocarbon system (including but not limited to a burial history, time a specific subsurface location or layer reached a certain temperature or maturity, or for how long a location was in a certain temperature range, timing of expulsion, migration, accumulation etc.). Generally a basin model is based on and/or constrained by measured or derived data representing present day conditions (e.g. stratigraphy, current bottom hole temperature, heat flow) or a condition in the past (e.g. water depth) on which a model of the past history of the area of interest is based. The calculations may be performed using a processor or other computer system.

As used herein, the term "signatures" refers to the relative abundances, concentrations and/or ratios of various elements, isotopes, positions within a compound and isotopologues of a given species.

As used herein, the term "isotopologue" refers generally to molecules that have the same chemical composition, but have a different isotopic signature. For example, methane contains one atom of carbon and four atoms of hydrogen. Each atom in the methane structure can contain one of the two stable isotopes of that atom, and as such there are ten possible isotopologues of methane.

As used herein, the term "multiply substituted isotopologue" refers generally to an isotopologue that contains at least two rare isotopes in its structure. For example, a multiply substituted methane isotopologue contains one $^{13}C$ atom and one D atom, or at least 2 D atoms in the absence of a $^{13}C$ atom.

As used herein, the term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

As used herein, the term "position specific isotope signature" refers generally to a compound that has multiple chemically or structurally distinct positions for a rare isotope to reside. For example, a position specific isotope effect in propane could refer to the position of the $^{13}C$ atom, which can be positioned either at the center of the compound or one of the end positions, or the position of the D atom, which can be attached to either a central or end position carbon.

As used herein, the term "stochastic distribution" refers generally to a system where the stable isotopes in a given population of molecules are distributed randomly among all possible isotopologues of a given species. This stochastic distribution is the reference frame from which deviations are measured and is used to provide a baseline to identify anomalies that may be associated with secondary isotope exchange processes.

According to aspects of the disclosed methodologies and techniques, the multiply substituted isotopologue or position specific isotope effects or signatures of single or numerous co-existing isotopologues of hydrocarbons can be integrated with results from basin modeling approaches to determine the timing of processes associated with the history of hydrocarbon compounds following generation for optimal prospect evaluation of larger volumes or higher quality of hydrocarbons for subsequent ranking and enhanced exploration success. In particular, these disclosed methodologies and techniques may be used to determine timing of processes such as (i) hydrocarbon generation, (ii) expulsion, (iii) migration, (iv) storage, (v) preservation, (vi) alteration, and (vii) mixing in hydrocarbon systems. Further, the disclosed methodologies and techniques may be used to determine one or more of historical temperature, type of alteration, and extent of alternation.

Any technique capable of providing this information may provide quantitative constraints on relative (and through integration with basin models potentially absolute timing) on processes (such as maturation, expulsions, migration, charge, preservation and/or alteration) to better predict the regional confluence of these different processes for optimal prospect evaluation of larger volumes or higher quality hydrocarbons for subsequent ranking and improved exploration, development and production success.

In one or more embodiments, the present techniques may include combining multiply substituted isotopologue signatures and position specific isotope effects of hydrocarbon compounds (e.g., $CH_4$, $C_2H_6$, $C_3H_8$) with elemental, molecular, and isotopic signatures obtained from gas, oil, water and fluid inclusion samples. The use of multiply substituted isotopologue and position specific isotope geochemistry may provide constraints on the historical temperature at which particular processes occur in hydrocarbon systems. When combined and integrated with traditional geochemical techniques, such as molecular (e.g., methane, ethane, carbon dioxide, nitrogen), bulk (e.g., mixtures of gases), stable isotope geochemistry (e.g., carbon, hydrogen, nitrogen, sulfur) of hydrocarbon and non-hydrocarbon gases, molecular geochemistry of oils (e.g., saturate and aromatic compounds), physical measurements (e.g., pressure, volume and temperature (PVT)), and results from basin modeling approaches; these techniques provide enhancements to technologies to quantitatively determine the timing of processes, such as the charging of subsurface structures with hydrocarbons or the alteration of hydrocarbons in these structures. The technology therefore provides a mechanism to alter exploration, development and production strategies to maximize the volume and quality of hydrocarbon ultimately produced.

Multiply substituted isotopologue geochemistry is based on the variation in the distribution of isotopes within a molecule that gives rise to molecules that are identical in their elemental composition, but that may differ in the isotopic composition of individual atoms within that molecule. These species are called isotopologues. For example, there are three isotopologues of nitrogen ($^{14}N_2$, $^{15}N^{14}N$ and $^{15}N_2$). An isotopologue in which two or more rare isotopes are present in close proximity (i.e., isotopic "clumps") is called a multiply-substituted isotopologue or clumped isotope (e.g., $^{15}N_2$). The hydrocarbon isotopologues involve hydrocarbon compounds (e.g., those that contain carbon and hydrogen atoms) that have natural isotopes of $^{12}C$, $^{13}C$, $^1H$, or H (deuterium or D). $^{12}C$ represents about 98.93 mole percent (mol. %) of the total carbon on Earth, while $^{13}C$ forms the remaining 1.07 mol. %. Similarly, the isotopic abundance of $^1H$ on earth is 99.985 mol. % while D has an abundance of 0.015 mol. %. Common volatile hydrocarbons have large numbers of isotopologues even considering only the stable isotopes (e.g., methane has 10; ethane has 36; propane has 216). Common isotopologues of methane for example include $^{13}C^1H_3D$ or $^{12}C^1H_4$. In addition to the number of rare isotopes, the distribution of isotopes in the molecule can also provide information. For example, in a linear hydrocarbon compound with three carbon atoms, the rare isotope can take either a central or terminal (end of the molecule) position. Similarly, rare isotopes of hydrogen can occupy different positions. As the size of the hydrocarbon compound increases, the number of positions that these rare isotopes can be situated increases. This effect is called the position specific isotope effect, or isotopomer geochemistry.

The multiply substituted isotopologue signature and the position specific isotope signature of any molecule is a function of (i) temperature-independent randomly populated processes (stochastic distribution) and (ii) other non-random mass fractionating processes. The stochastic distribution of any isotopologues can be determined from the bulk isotope signatures of the species from which it derives. For example, determining the stochastic distribution of isotopologues for methane involves knowledge of the $^{13}C$ and D signatures of methane. At equilibrium, a non-stochastic distribution may result from thermodynamic differences between the different isotopologues. Under non-equilibrium conditions, the non-random processes may be temperature-time dependent isotopic exchange reactions in some hydrocarbons. For example, multiply substituted isotopologue signatures in methane appear to provide equilibrium gas generation temperatures see, e.g., Stolper, D. A. et al., (2014), "Formation temperatures of thermogenic and biogenic methane", Science, Vol. 344, pp. 1500-1503. Additional equilibrium or non-equilibrium kinetic isotope exchange processes may also influence the signatures in some hydrocarbon species. These processes may include, but are not limited to, biodegradation, secondary thermal cracking of hydrocarbons, thermochemical oxidation/reduction reactions, mixing or diffusion, etc. These processes may differ in their relative magnitude of the impact on the multiply substituted isotopologue signatures and/or position specific isotope signatures. In addition to the size of the signatures, the time required for these processes to affect the signature may also differ from compound to compound. Integration of measured multiply substituted isotopologue signatures and position specific isotope signatures of multiple hydrocarbon species with an understanding of the kinetic properties of these species provides unique constraints on both the temperature at which hydrocarbons are generated and/or stored in the subsurface and the length of time for which the hydrocarbons have been stored. Kinetic properties of multiply substituted isotopologue signature and isotope position specific signatures may be derived from laboratory experiments or modeling approaches.

For example, some species may develop a signature that does not change over timescales of billions of years if conditions or reactions change. One example of this may be methane, which appears to develop a multiply substituted isotopologue signature that is dominantly sensitive to temperature. This signature appears to develop during generation of the methane, and is then locked in even if the methane is transported to a colder environment and stored (see, e.g., Stolper, D. A. et al., (2014), "Formation temperatures of thermogenic and biogenic methane", Science, Vol. 344, pp. 1500-1503). In contrast, other molecules that are sensitive to temperature may track changes in temperature over short timescales. For example, decane may initially develop a signature that records the temperature at which it was generated, but this signature may subsequently change to reflect increases or decreases in the temperature at which the compound resides over timescales of years. Another example may be that some isotopologues, multiply substituted isotopologue or positions within molecules may be sensitive to biodegradation, which may give rise to signatures that can be used to determine the extent of biodegradation and, if an understanding of the time taken to biodegrade the particular compound is possible, how long the hydrocarbon has been undergoing biodegradation. By measuring the clumped and position specific isotope signatures of multiple hydrocarbon compounds that may be sensitive to different parameters and may have different rates of reaction, different information about the history of the hydrocarbons may be determined following generation. The hydrocarbon generation, entrapment and/or alteration temperatures derived from the measured signatures are then integrated with a basin model of the area of interest within the subsurface, which can be used to constrain the times or timescales over which these processes occurred. Various aspects of the present techniques are described further in FIGS. 1 to 7.

FIG. 1 is a side elevational diagram 100 of components of a hydrocarbon system in a subsurface region. In this diagram 100, components and events in a hydrocarbon system are provided for a subsurface region 102, which may be at least partially below a body of water 104. The processes of a hydrocarbon system involve generation, migration, trap formation, accumulation or leakage to a seep, and/or preservation. The elements (or components) of the hydrocarbon system include various portions of a formation, such as source rocks 106, reservoir rocks 108 and seal rocks 110. Hydrocarbon systems analysis may involve determining source presence, source maturation, trap presence, migration pathways, reservoir presence, trap seal presence and timing. The hydrocarbons may be produced through a wellbore 126.

As an example, the hydrocarbon system process may involve various steps to form current hydrocarbon locations. First, hydrocarbons are generated, which occurs in source rock 106. Then, the hydrocarbons migrate from the source rock 106 through faults and fractures, such as fractures 111, as shown by arrows 112, 114, 116 and 118. Hydrocarbons accumulate in a reservoir. Accumulation of hydrocarbons can only occur if a trapping structure is present at the same time or before hydrocarbons migrate through the reservoir rock 108 if an adequate seal rock 110 is in place. Hydrocarbons can be stored in an accumulation and preserved, as shown by the seal rocks 110 or may be altered by a fracture, as shown by fault 120. If limited by subsurface geology, the hydrocarbons may be trapped in hydrocarbon accumulations, such as a gas reservoir and/or an oil/gas reservoir. Hydrocarbons may seep into the body of water 104 via the fault 120, as shown by bubbles 122, and form an oil slick 124 on the surface of the body of water 104.

The historical temperatures derived from multiply substituted isotopologue signatures and/or position specific isotope signatures measured for any given hydrocarbon compound may represent (i) the historical temperature at the hydrocarbon compound was generated if the compound has experienced a different temperature for a period of time that is small relative to the rate at which it undergoes equilibration, (ii) the ambient temperature at which it resides if the compound is sensitive to equilibration over timescales that are less than the time at which it has been at ambient temperature, or (iii) some other temperature if the compound has not yet reached equilibrium following generation. A historical temperature at which any given process (such as biodegradation) has occurred or any point in time in the hydrocarbon compound history can be determined using mathematical techniques that consider the time-temperature history of the depth at which the hydrocarbon has resided and the rate and sensitivity of the compound to equilibration.

Figure 2:
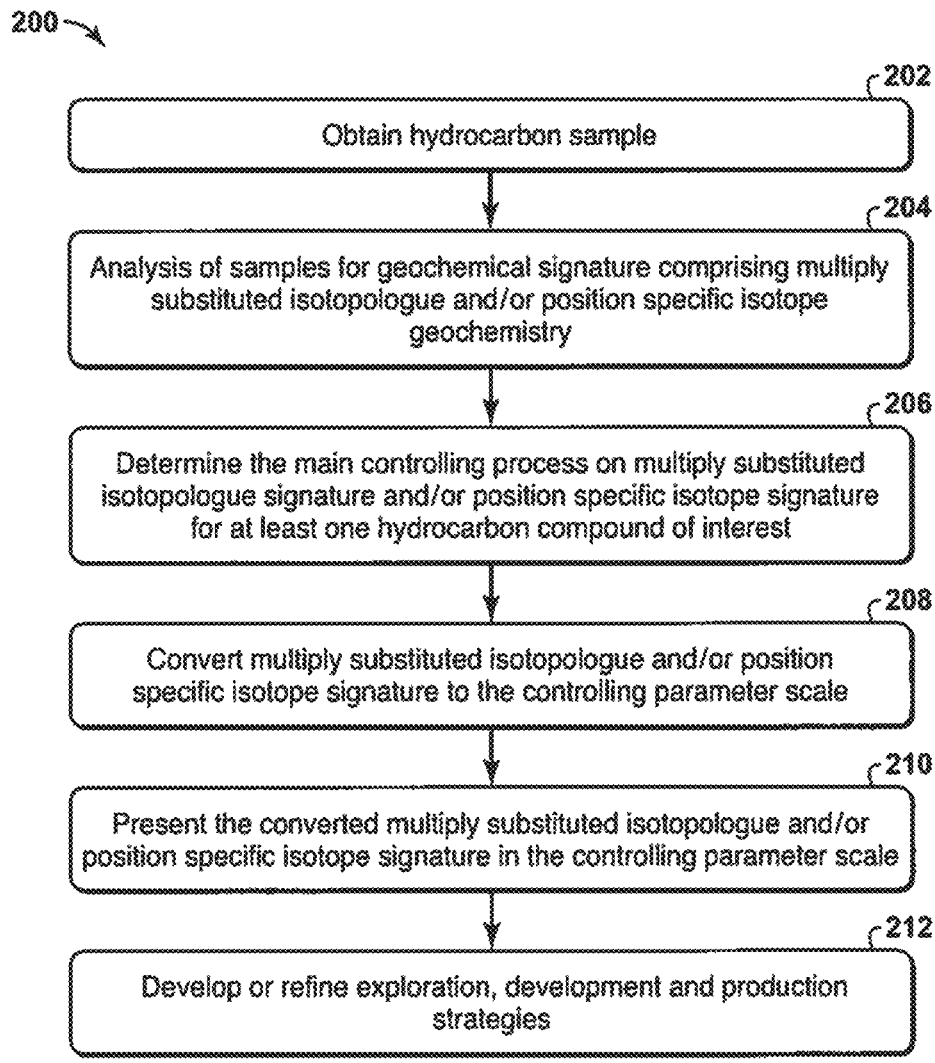
FIG. 2 is a flow diagram of an exemplary method to determine process(es) controlling the measured multiply substituted isotopologue or position specific isotope signatures of any given hydrocarbon in accordance with an exemplary embodiment of the present techniques.

FIG. 2 is a flow diagram 200 of an exemplary method to determine process(es) controlling the measured multiply substituted isotopologue or position specific isotope signatures of any given hydrocarbon in accordance with an exemplary embodiment of the present techniques. In this diagram 200, this approach may be used to identify compounds whose multiply substituted isotopologue signature and/or position specific isotope signature are controlled only or primarily by temperature (e.g., an equilibrium signature that is predictable from molecular modeling). This signature may or may not be in equilibrium with the current environmental temperature. For example, a compound may be controlled by temperature, but the compound may not have been stored at the current temperature for a sufficient period of time to allow the signature to equilibrate to ambient. In such an example, the signature may lie somewhere between a generation temperature and current ambient temperature. Alternatively, the multiply substituted isotopologue signature and/or position specific isotope signature may be controlled by other equilibrium or non-equilibrium processes such as alteration (e.g., biologic degradation, thermal cracking, oxidation and the like).

At block 202, a sample of hydrocarbons is obtained. This sample can be in the form of oil and/or gas obtained from the subsurface, at a surface location, such as a seep, and may be in the form of free oil and/or gas, as solid hydrocarbons, or may be trapped within a rock sample.

At block 204, the samples may be analyzed for geochemical signature, which may include multiply substituted isotopologue and/or position specific isotope geochemistry. If methane, the primary chemical component of natural gases, is used as an example, it is possible to investigate the potential of forming the clumped doubly substituted isotopologue $^{13}CH_3D$, and the doubly substituted isotopologue $^{12}CH_2D_2$. This analysis may also include a variety of geochemical signatures comprising bulk composition, isotopic signatures, molecular geochemistry, and physical parameters such as freezing or boiling points of a given compound, which may be used to provide additional information, such as source facies. The sample may be analyzed for its multiply substituted isotopologue signature and or position specific isotope signature. The measurement of the absolute abundance of isotopologues or position of interest for any given hydrocarbon requires knowledge of the molecular mass at which they are present, and hence requires knowledge of the actual identity of each possible isotopologue for that species. Measurement of the abundance of each isotopologue or fragment can be conducted using multiple techniques, such as mass spectrometry and/or laser-based spectroscopy.

Then, at block 206, the main controlling process on multiply substituted isotopologue signature and/or position specific isotope signature for at least one hydrocarbon compound of interest is determined. The parameter controlling the multiply substituted isotopologue or position specific isotope signatures may be determined through various methods. For example, the determination may be performed by first assessing the impact of temperature on the measured signatures. Temperature is an equilibrium signature that can be predicted by molecular modeling of equilibrium concentrations of multiply substituted isotopologue or positional effects, or may be determined empirically by measurements of signatures of a given hydrocarbon compound at different temperatures either in the presence or absence of a catalyst to accelerate equilibrium. Different hydrocarbon species have different rates of equilibration of their multiply substituted isotopologue and position specific effects. For example, the $^{13}CH_3D$ isotopologue in methane may record methane generation temperature (see e.g., Stolper, D. A. et al., (2014), "Formation temperatures of thermogenic and biogenic methane", Science, Vol. 344, pp. 1500-1503.) and preserves the signature even when exposed to different temperatures during migration or uplift of the sediments in which the methane is contained. In contrast, a molecule, such as decane, may give a historical temperature that reflects the temperature at which it has been stored over the past several years because it may undergo intra-molecular isotope exchange over faster timescales than methane. Temperatures obtained from the clumped or position specific isotope signatures may be different for different species because each of these hydrocarbon compounds record different parts of the history of the bulk hydrocarbon given their different kinetic behaviors.

If the signature is shown to be outside the range of an equilibrium signature, or appears to be unrelated to temperature, then other fractionating processes should be considered. These may include alteration processes, such as biodegradation, secondary cracking of hydrocarbons, or other processes.

The process controlling the multiply substituted isotopologue or position specific isotope signature may be determined through molecular modeling approaches, through experimentation or empirical observations. One example may be to use molecular modeling approaches that predict the impact of multiply substituted isotopologue signatures as a function of increasing alteration for any given process. For example with biodegradation, a molecular model can determine the impact of variable levels of biodegradation when molecules likely to be impacted by biodegradation are known. For example, methane is not thought to be altered by biodegradation other than by receiving methane as a bi-product of the process. In contrast, propane is known to be a compound that can be altered by biodegradation. A model can therefore be developed to predict the impact of any given alteration process (in this example biodegradation) on particular isotopologues of the hydrocarbon compound of interest (e.g., propane), or on particular position specific effects in the hydrocarbon compound.

Another example may be to experimentally determine the impact of a process on a hydrocarbon compound of interest in the laboratory. Using biodegradation again as an example, a hydrocarbon compound (for example propane) may be exposed to micro-organisms known to degrade the compound for different periods of time to produce propane that has experienced different levels of biodegradation. This propane could then be analyzed for its multiply substituted isotopologue or position specific isotope signatures to develop a model for how propane signatures evolve as a function of any given process.

Another example may be to compare the multiply substituted isotopologue or position specific isotope signature to data from empirical observations of other data sets for the same compound when the process controlling its signature is well known. For example, one may compare the multiply substituted isotopologues or position specific signature of propane from the sample taken in block 202 with databases of samples previously analyzed from different locations that have experienced different alteration processes and at different levels of alteration. Once the signatures from block 202 are shown to match a process from the database, the database may be used to define a model for determining the extent of that process.

Given sufficient time and the availability of relevant pathways, the atoms in a population of molecules may redistribute to achieve their most stable, or equilibrium, state at the prevailing conditions. This state may differ from the stochastic state described previously, though it may approach it, which depends on the system, as the temperature is increased. For historical temperatures relevant to hydrocarbon systems analysis, the distribution of isotopologues may differ from the stochastic and the distribution or its difference from the stochastic may reflect the temperature at which equilibrium was achieved. From previous experimental and theoretical studies, it is known that the relationship between the distribution and temperature is usually monotonic, so that given an equilibrium distribution, a single temperature can be inferred if the relationship is known for the molecular species of interest. For example, the relative population of the isotopologues of methane can be equilibrated in a few hours at 200 less than or equal to (<=) T(C)<=600 in the presence of a Nickel catalyst and the ratio of $^{13}C^1H_3D$ and $^{12}C^1H_2D_2$ to $^{12}C^1H_4$ molecules is indicative of the actual temperature of the experiment (See, e.g., Stolper D. A., et al., (2014), "Combined $^{13}C$-D and D-D clumping in methane: Methods and preliminary results", Geochimica et Cosmochimica Acta, Vol. 126, pp. 169-191).

The application of multiply-substituted isotopologue signatures to determine temperatures involves the equilibrium relationship being known. This can be determined in several methods, which include experimental information, theoretical or computed information, and a combination of both. First, as in the above example regarding methane, laboratory experiments which measure the temperature and the compositions at equilibrium are both determined. The compositions are combined into approximate (ideal gas) equilibrium "constants" (they vary with temperature, but not pressure or composition), which can then be used along with bulk compositional information (D/H, $^{13}C/^{12}C$), to determine the equilibrium isotopic composition for any temperature or the temperature for any equilibrium composition. The experimental determination of the distribution of isotopologues can be determined in the laboratory by any method or methods commonly used to measure composition, such as mass spectrometry, infrared and/or Raman spectroscopy, gas chromatography, nuclear magnetic resonance, etc. Isotopically labeled species can be used, increasing the overall amounts of rare isotopes so that the concentrations of naturally rare species can be measured more accurately.

Other than direct measurement of compositions, the equilibrium constants can be determined using properties of the individual isotopologues and the equations of statistical mechanics. See, e.g., D. MacQuarrie, Statistical Mechanics, University Science Books, pp. 113-159, (2000). The equations of statistical mechanics relate properties of the individual molecules (e.g., vibrational frequencies, moments of inertia, etc.) to partition functions (or partition function ratios) and the partition functions (or ratios) of a collection of molecules related via a chemical or isotopic transformation equation to the equilibrium constants. Of course there are various approximations available in statistical mechanics and different combinations of different properties of the molecules may be used to determine the partition functions or partition function ratios.

The most common historically-used method uses experimentally measured vibrational frequencies from infrared and/or Raman spectroscopy and other molecular properties inferred from those spectroscopies. These methods are known in the art. See e.g., Urey, H. C., et al., "Some Thermodynamic Properties of the $H^1H^2$, $H^2H^2$ Molecules and Compounds Containing the $H^2$ Atom", J. Chemical Physics, Vol. 1, pp. 137-143 (1933); Bigeleisen and Mayer, "Calculation of Equilibrium Constants for Isotopic Exchange Reactions", J. Chem. Phys., Vol. 15, No. 5, pp. 261-267, (1947); and Richet, Bottinga, and Javoy, "A Review Of Hydrogen, Carbon, Nitrogen, Oxygen, Sulphur, And Chlorine Stable Isotope Fractionation Among Gaseous Molecules", Annual Reviews In Earth and Planetary Sciences, Vol. 5, pp. 65-110 (1977). These methods use only the relatively few fundamental vibrational frequencies of the molecules, or the related harmonic frequencies (which are properties of the potential energy surface of the molecules and which are inferred from the experimental frequencies and other molecular properties). A related method, less dependent on approximations, uses substantially experimental information by directly summing partition function components from hundreds or thousands of vibrational/rotational spectroscopic lines. An example of such a method on the water molecule is provided by M. Vidler and J. Tennyson, "Accurate partition function and thermodynamic data for water", J. Chem. Phys., Vol. 113, No. 21, pp. 9766-9771 (2000).

For convenience and because of the difficulty of obtaining accurate experimental information on the various isotopologues of a given molecular species, modern quantum chemical calculations may also be used to provide the molecular properties, which are combined with statistical mechanical equations to yield partition functions, partition function ratios, and/or equilibrium constants. Often, similar or the same statistical mechanical equations are used as in the above methods, but the molecular properties and frequencies are calculated from quantum chemical methods. The most computationally efficient and commonly applied approach is to use the Urey or Bigeleisen-Mayer methods and to calculate "harmonic frequencies". These are frequencies, which are calculated from a harmonic oscillator (quadratic potential function) approximation of the interatomic potential energy surface of the molecules. Several points on the potential energy surface are calculated directly from quantum chemical methods. Potentially more accurate results for the partition functions and equilibrium constants can be generated using computed anharmonic frequencies (which correspond to measured fundamental frequencies) and other properties of the molecules and their potential energy surfaces. See, e.g., Liu et al., "On the proper use of the Bigeleisen-Mayer equation and corrections to it in the calculation of isotopic fractionation equilibrium constant", Geochimica et Cosmochimica Acta, Vol. 74, pp. 6965-6983 (2010). For some more complex molecules, physical and computational effects such as "resonance" are known to degrade the quality of the computed properties. These can partially be corrected using the methods discussed in Bloino et al., and as implemented in commercial quantum chemistry software. See e.g., J. Bloino, M. Biczysko, and V. Barone, "General Perturbative Approach for Spectroscopy, Thermodynamics, and Kinetics: Methodological Background and Benchmark Studies", J. Chem. Theory Comput., Vol. 8, pp. 1015-1036 (2012).

As an example, the methods of Bloino et al. may be used in the Gaussian 09 software (e.g., Gaussian 09, Revision D.01, Frisch et al., Gaussian, Inc., Wallingford Conn. (2009)) combined with the B3LYP density functional method or MP2 post-Hartree Fock ab initio method and the aug-cc-PVTZ basis set to compute anharmonic frequencies and other molecular constants for methane. These can be used with the simple perturbation theory of Truhlar et al. to provide partition functions and these combined to produce equilibrium constants. See, e.g., Truhlar, D. G. and Isaacson, A. D., "Simple perturbation theory estimates of equilibrium constants from force fields", J. Chem. Phys., Vol. 94 (1), pp. 357-359 (1991). Equations involving the equilibrium constants and the bulk isotopic signatures for $^{13}$C and D can be solved using standard linear equation solvers in a package such as Matlab (see, e.g., MATLAB, The MathWorks, Inc., Natick, Mass., United States)

Other computational methods may be used to provide some or all of the information involved in predicting partition functions and equilibrium constants. For example, path integral Monte Carlo methods may be used. These have been applied to isotopic fractionation in methane and other molecules by Webb and Miller. See M. A. Webb and T. F. Miller, III, "Position-Specific and Clumped Stable Isotope Studies: Comparison of the Urey and Path-Integral Approaches for Carbon Dioxide, Nitrous Oxide, Methane, and Propane", J. Phys. Chem. A, Vol. 118, pp. 467-474 (2014). Ab initio Molecular Dynamics has been used to account for the influence of solvent fluctuations on isotopic fractionation by Rustad et al. See J. R. Rustad, E. J. Bylaska, V. E. Jackson, and D. A. Dixon, "Calculation of Boron-Isotope Fractionation Between $B(OH)_3$(aq) and B(OH)-(aq)", Geochimica et Cosmochimica Acta, Vol. 74, pp. 2843-2850 (2010).

Various options are available for the approximations and equations used from statistical mechanics. Similarly, there is a large variety of "model chemistries", which may be used to provide useful estimates of the molecular properties from computational quantum chemistry. The different methods may be distinguished by the use of ab initio theory or density functional theory. The methods may also be distinguished by different prescriptions for various physical and theoretical effects, such as electron exchange and correlation. The selection of a "basis set" to describe the possible states of electrons may be useful. Different methods and equations may be chosen for computing an harmonically-corrected molecular properties and for dealing with various forms of resonance interactions. The optimal combination of methods may depend on the accuracy desired, the software and computer hardware available, and the specific molecular systems of interest.

Position-specific isotope signatures are different than effects due to multiply substituted isotopologue signatures (e.g., multiple substitutions of rare isotopes), but may be combined with other effects. The same theoretical and computational methods may be used to compute partition functions and equilibrium constants for position-specific isotopologues and their conversion reactions. Experimentally, some methods are not able to differentiate between position-specific isotopomers. For example, mass spectral methods that rely only on the parent molecular ion do not contain useful information on the position of the different isotopic atoms. However, fragments of the molecular ion may contain such information. The mass spectrum signals due to $C_2H_5^+$ and $CH_3^+$ fragments of propane (and their $^{13}$C and D containing forms) are related to the relative amounts of the position specific forms of propane; e.g. $(H_3C)(CHD)(CH_3)$ vs. $(H_3C)(CH_2)(CH_2D)$.

As an example, Wang et al. describes calculations of partition function ratios and fractionation factors for various positions in various functional groups for hydrocarbons and other organic molecules using density functional theory with the B3LYP functional and the 6-311G** basis set with further calibration to experiments on rapidly exchanging hydrogen positions adjacent to the carbonyl group in ketones. See, e.g., Y. Wang, A. L. Sessions, R. J. Nielsen, and W. A. Goddard, "Equilibrium $^2$H/$^1$H fractionations in organic molecules: I. Experimental calibration of ab initio calculations", Geochimica et Cosmochimica Acta, Vol. 73, pp. 7060-7075 (2009).

Time-dependent behavior of multiply substituted isotopologues and position specific isotope effects arise because not every natural process achieves equilibrium, even over geologic time-scales. Because chemical reaction rates generally decrease with temperature, for some processes, there exist "closure" or "blocking" temperatures. That is, closure or blocking temperatures are temperatures above which equilibrium is achieved on the time-scales of interest for a particular application, and below which equilibrium is not achieved on the time-scales of interest. For hydrocarbon systems analysis, if a sample which includes hydrocarbons and related molecular species, is cooled from some initially high temperature, the system may achieve equilibrium at a relatively high temperature, but this equilibrium may be 'frozen-in' at the blocking temperature and subsequent cooling does not re-set this equilibrium. The characteristic temperature determined from multiply-substituted, clumped, or position-specific effects on a particular molecular type may then indicate this blocking temperature.

In the present techniques, these effects are exploited for hydrocarbon systems analysis. In the present techniques, a plurality of molecular species present in a sample each have different blocking temperatures and measurement of their isotopic signatures that can provide information about the thermal history of the sample.

Methods used to determine the rates and temperature-dependence of isotope exchange reactions are related to those used to determine equilibrium. Note that kinetic isotope effects may also provide information, but it is not the variation of exchange rates between different isotopologues that is primarily of interest. That is, the overall time-scale of interconversion as a function of temperature provides useful information. The methods of measuring chemical rates is known in the art. One of the difficulties that has to be overcome in the experimental determination of rates as applied to geochemical processes is that those processes may effectively occur over geological time-scales, but not occur over laboratory time-scales. Sometimes increased temperatures are used to increase the rates into a measurable range and then an attempt is made to extrapolate the rates to the geological temperatures of interest. For example, the rates of hydrogen-isotope exchange reactions in hydrocarbons were investigated by Reeves et al. See, e.g., E. P. Reeves, J. S. Seewald, S. P. Sylva, "Hydrogen isotope exchange between n-alkanes and water under hydrothermal conditions", Geochimica et Cosmochimica Acta, Vol. 77, pp. 582-599 (2012). This extrapolation may be inaccurate and in addition, the relative rates of different processes may be different at different temperatures. For these reasons and others, the theoretical and/or computational approaches may be used to determine estimates of rates.

Methods of computing estimates of rates are also well known in the art. See, e.g., Transition State Theory, S. Glasstone, K. J. Laidler, and H. Eyring, "The Theory of Rate Processes", McGraw-Hill, New York (1941). The estimates may be less accurate than those of isotopic equilibrium phenomena (e.g., may only be accurate to within an order of magnitude), but the estimates may be useful for establishing approximations to blocking temperatures. Many of the same choices of methods and parameters that are be made in computing equilibrium properties are necessary in computing rates via computational chemistry methods.

In block 208, the multiply substituted isotopologue signature and/or position specific isotope signature may be converted into the controlling parameter scale (e.g., temperature scale, biodegradation scale, etc.). For example, the signature measured in block 204 may be converted to a parameter and quantified indices. In particular, if temperature is shown to be the primary process controlling the signature, then the signature is converted to a given temperature (e.g., in degrees Celsius) for the compound of interest. As another example, if the controlling process is biodegradation, the measured signature is converted to some indices of biodegradation and a quantification of the level of biodegradation (e.g., 80% completion of biodegradation of propane). The knowledge of the extent of biodegradation may influence where the exploration, development and production operations are targeted.

Then, in block 210, the multiply substituted isotopologue signature and/or position specific isotope signature is presented in the controlling parameter scale. The presentation of the controlling parameter scale may include displaying the multiply substituted isotopologue signature and/or position specific isotope signature in the temperature scale or biodegradation scale, for example.

At block 212, exploration, development and production strategies may be developed or refined. This development or revision is based on the multiply substituted isotopologue signature and/or position specific isotope signature presented in the controlling parameter scale.

Figure 3:
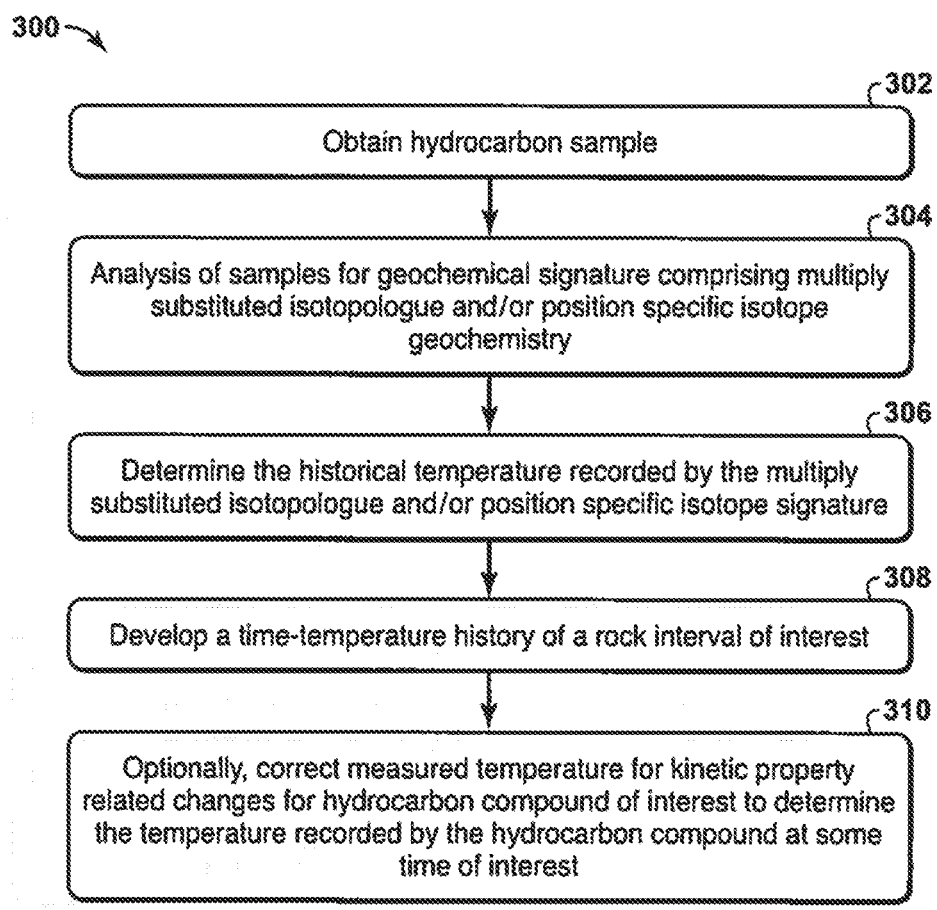
FIG. 3 is a flow diagram of an exemplary method to calculate a historical temperature at any given time in the hydrocarbon compounds history from measured multiply substituted isotopologue or position specific isotope signatures in accordance with an exemplary embodiment of the present techniques.

FIG. 3 is a flow diagram 300 of an exemplary method to calculate a historical temperature at any given time in the hydrocarbon compounds history from measured multiply substituted isotopologue signature and/or position specific isotope signatures in accordance with an exemplary embodiment of the present techniques. In this diagram 300, the method may be used to calculate the initial temperature of a process or time of interest from measured multiply substituted isotopologue signature and/or position specific isotope signatures. Further, this method may be used to determine the temperature present day or a historic temperature of the hydrocarbon (e.g., at the time of maximum burial or when hot, hydrothermal fluids passed through the rocks associated with some geologic event) for any given hydrocarbon compound.

The method begins at block 302. In block 302, a sample of hydrocarbons is obtained. Similar to block 202 of FIG. 2, this sample may be in the form of oil and/or gas obtained from the subsurface or at a surface location, and may be free oil, free gas or trapped within a rock sample.

At block 304, the sample is analyzed for geochemical signatures, which include multiply substituted isotopologue and/or position specific isotope geochemistry. This analysis may be similar to the analysis of block 204 of FIG. 2. This analysis may also include a variety of geochemical signatures comprising bulk composition, isotopic signatures, molecular geochemistry, and physical parameters such as freezing or boiling points of a given compound that provide additional information on the origin or history of the hydrocarbons. If methane, the primary chemical component of natural gases, is used as an example, it is possible to investigate the potential of forming the clumped doubly substituted isotopologue $^{13}CH_3D$, and the doubly substituted isotopologue $^{12}CH_2D_2$. The measurement of the absolute abundance of isotopologues for any given hydrocarbon involves knowledge of the molecular mass at which they are present, and involves knowledge of the actual identity of each possible isotopologue for that species. Measurement of the abundance of each isotopologue and fragment for position specific isotope determination can be conducted using multiple techniques, such as mass spectrometry and/or laser-based spectroscopy.

Then, at block 306, the historical temperature recorded by the multiply substituted isotopologue signature and/or position specific isotope signature is determined. The historical temperature recorded by the multiply substituted isotopologue signature and/or isotope position specific isotope signatures is determined for any given hydrocarbon that is known or believed to be controlled by temperature at block 306. Temperature is an equilibrium signature that can be predicted by molecular modeling of equilibrium concentrations of multiply substituted isotopologue or positional effects, or may be determined empirically by measurements of signatures of a given hydrocarbon compound at different temperatures either in the presence or absence of a catalyst to accelerate equilibrium. Different hydrocarbon species have different rates of equilibration in multiply substituted isotopologues. For example, methane records methane generation temperature and preserves this signature even when exposed to different temperatures. In contrast, a molecule such as decane may give a temperature that reflects the temperature at which it has been stored over the past several years because it can undergo intra-molecular isotope exchange over faster timescales than methane. Historical temperatures obtained from the clumped or position specific isotope signatures may be different for different species because each of these hydrocarbon compounds record different parts of the history of the bulk hydrocarbon given their different kinetic behaviors.

In block 308, a time-temperature history is developed for a rock interval of interest. For example, the time-temperature history for a source rock interval where hydrocarbons are generated or of a reservoir rock interval where hydrocarbons are hosted may be determined. Time-temperature histories can be developed for a given rock interval from approaches, such as basin modeling. These models are typically calibrated with direct temperature information (e.g., from fluid inclusion temperatures) or indirect maturity information (e.g. vitrinite, molecular geochemistry, etc.), thicknesses and lithologies for depth intervals in the subsurface, some estimation of paleo-water depth, and basal heat flow estimates. That is, the time-temp history is developed independently, but may be used to correct for changes in a compound because of changes in temp over a period of time.

In block 310, a measured temperature of a hydrocarbon compound with a known related kinetic property may be used to determine a correct a measured temperature for kinetic property related changes for hydrocarbon compound of interest to determine the historical temperature recorded by the hydrocarbon compound at some time of interest may optionally be determined. For example, the signature and temperature determined in blocks 304 and 306 can be used with the time temperature history for a given rock in 308 with knowledge of the kinetic sensitivity of any given hydrocarbon compound to equilibrate at different temperatures to determine what temperature may be recorded in any given compound at any time of interest. For a compound, such as methane, that does not appear to equilibrate on geologic timescales, the temperature measured present day is likely to be the same as the temperature that may be measured at any time following generation, assuming that the gas is sourced from one location and has not mixed or undergone any bio or geochemical reactions. For a compound that may equilibrate over relatively rapid timescales, for instance over thousands of years, the temperature recorded by the measured multiply substituted isotopologue or position specific isotope signature present day is likely to be different to that which may be recorded by the same compound 1 million years ago. For example, to determine the temperature recorded by a multiply substituted isotopologue signature and/or position specific isotope signature of pentane 1 million years ago, the measured signature recorded in block 304 may be corrected for any change in its signature associated with its time-temperature history determined in block 308.

The kinetic properties for different hydrocarbon compounds can be determined through different approaches. One approach may be to determine kinetic parameters experimentally. This can be done, for example, by subjecting any hydrocarbon compound to a range of temperatures with or without the presence of a catalyst for different periods of time. See, e.g., Stolper, D. A. et al., (2014), "Formation temperatures of thermogenic and biogenic methane", Science, Vol. 344, pp. 1500-1503. The hydrocarbon compounds taken from these different experiments are analyzed and its kinetic properties can be determined for any given temperature based on how quickly equilibration is reached at different temperatures in each experiment.

An alternative approach may be to use molecular modeling to predict the timescales at which the multiply substituted isotopologue signature and/or position specific isotope signature of any given hydrocarbon compound.

Based on data from either of these different approaches, a model can be developed to provide kinetic parameters for any hydrocarbon compound. From this model, a present day signature can be corrected for any historical change in its signature based on changes in temperature over some period of time to determine the signature, and from this a historical temperature, for any hydrocarbon compound for any time of interest.

Figure 4:
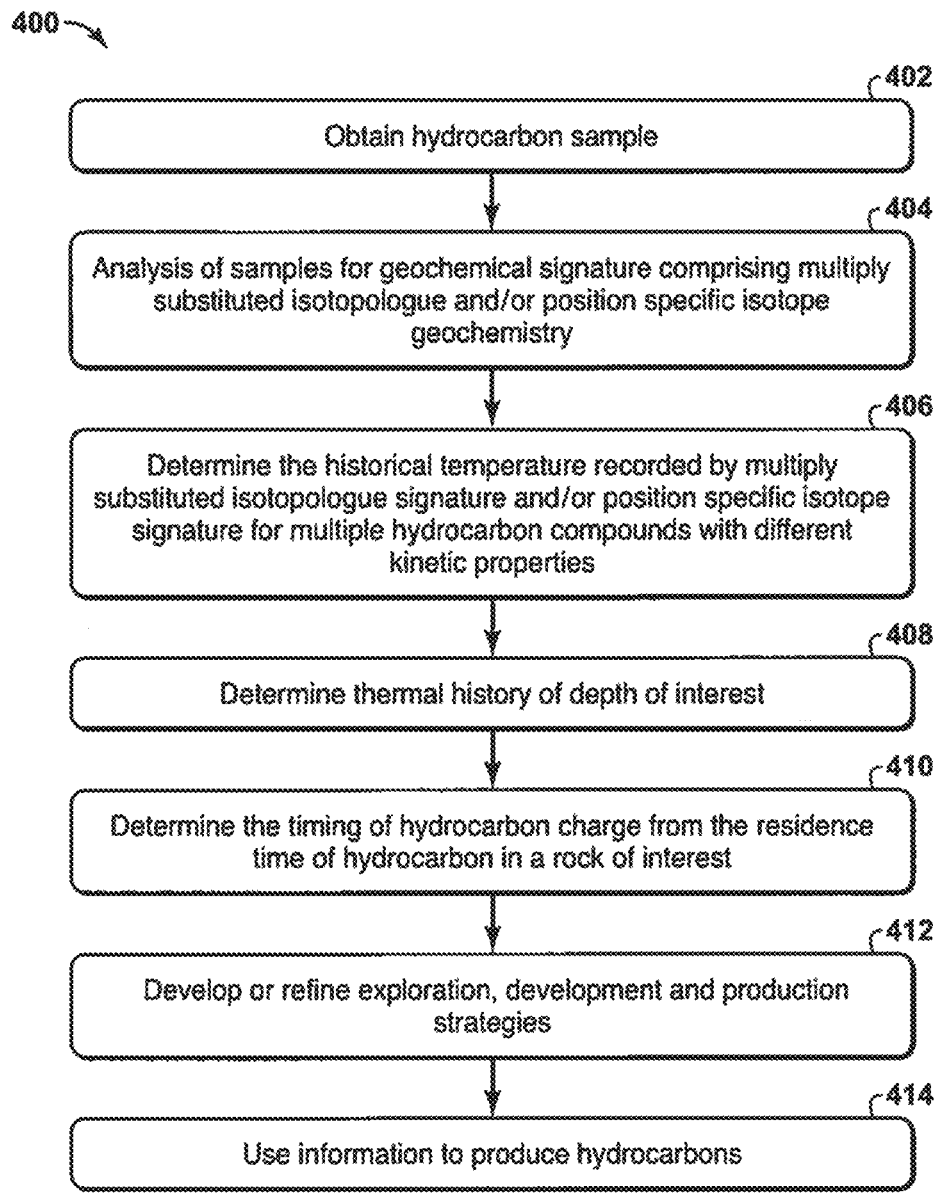
FIG. 4 is a flow diagram of an exemplary method to determine charge timing of hydrocarbons in an accumulation in accordance with an exemplary embodiment of the present techniques.

FIG. 4 is a flow diagram 400 of an exemplary method to determine charge timing of hydrocarbons in an accumulation in accordance with an exemplary embodiment of the present techniques. In this diagram 400, charge timing of hydrocarbons in an accumulation may be determined.

The method begins in block 402. At block 402, a sample of hydrocarbons is obtained. Then, at block 404, the sample is analyzed for multiply substituted isotopologue signature and/or position specific isotope geochemical signatures. This obtaining the hydrocarbon sample may be similar to the discussion of block 202 of FIG. 2 and block 302 of FIG. 3, while the analysis of the samples may be similar to the discussion of block 204 of FIG. 2 and block 304 of FIG. 3.

In block 406, the historical temperature recorded by the multiply substituted isotopologue signature and/or position specific isotope signatures is determined for multiple hydrocarbon compounds with different kinetic properties. This determination may be performed similar to that in block 306 of FIG. 3. Further, this may be corrected by additional property information for the different hydrocarbons.

In block 408, a thermal history of depth of interest is determined. The time-temperature history for a given depth of interest may be determined from basin modeling and other approaches. The basin models may be calibrated with direct temperature information (e.g., from fluid inclusion temperatures) or indirect maturity information (e.g., vitrinite, molecular geochemistry etc.), thicknesses and lithologies for depth intervals in the subsurface, some estimation of paleo-water depth, and basal heat flow estimates.

In block 410, the timing of hydrocarbon charge from the residence time of hydrocarbon in a rock of interest is determined. This timing may be determined from the measured temperature determined in block 406, which is used to determine the residence time of a hydrocarbon compound in a given rock. This can be performed using multiple approaches. One example may be to compare the temperatures provided by different hydrocarbon compounds that have different kinetic properties in block 406 to find multiple compounds that provide the same temperature and one species that provides a different temperature. For example, from the same sample, if a first compound equilibrates in one million years, a second compound in five hundred thousand years, a third compound in one hundred thousand years, and a fourth compound in fifty thousand years, and if the second, third and fourth compounds record a temperature of 80 degrees Celsius and the first compound records a temperature of 120 degrees Celsius, then the hydrocarbon has been stored at 80 degrees Celsius for at least five hundred thousand years, but not as long as one million years.

An alternative approach may be to use a statistical approach that considers the signatures of two compounds with different kinetic properties that record the same temperature and at least two compounds with different kinetic properties that record independently different temperatures alongside the time-temperature history developed in block 408. From this, it is possible to calculate an absolute residence time (or time since which the hydrocarbon has been stored) from the different multiply substituted isotopologue or position specific isotope signatures and the kinetic properties of different compounds by considering the impact of the time-temperature history of the rock in which these hydrocarbons were stored.

The residence time determined from block 410 represents the time at which hydrocarbons initially charged the rock in which they are stored.

In block 412, exploration, development and production strategies may be developed or refined. The development or refinement of the exploration, development and production strategies may be based on the information determined in blocks 404 to 410. For example, the information obtained in block 410 is used to develop or refine an exploration, development and production strategy. In particular, the information about when hydrocarbons are charging particular structures may be used to enhance predictions of the regional confluence of the timing of hydrocarbon generation, trap and seal timing and hydrocarbon charge for optimal evaluation of other prospects on a local or regional scale to enhance subsequent ranking of prospects and ultimately improve exploration, development and production success by finding larger volumes of hydrocarbons, higher quality hydrocarbons and/or lessening uncertainty associated with the hydrocarbons.

The strategies may then be used to produce hydrocarbons from subsurface accumulations in block 414. Producing hydrocarbon may include operations, such as modeling the location to drill a well, directing acquisition of data for placement of a well, drilling a well, building surface facilities to produce the hydrocarbons, along with other operations conducted in and/or associated with the well after the well is completed. Accordingly, producing hydrocarbons includes hydrocarbon extraction, along with injection of gas or liquid for increasing drive pressure, mobilizing the hydrocarbon or treating by, for example chemicals or hydraulic fracturing the wellbore to promote increased flow, well servicing, well logging, and other well and wellbore treatments.

Figure 5:
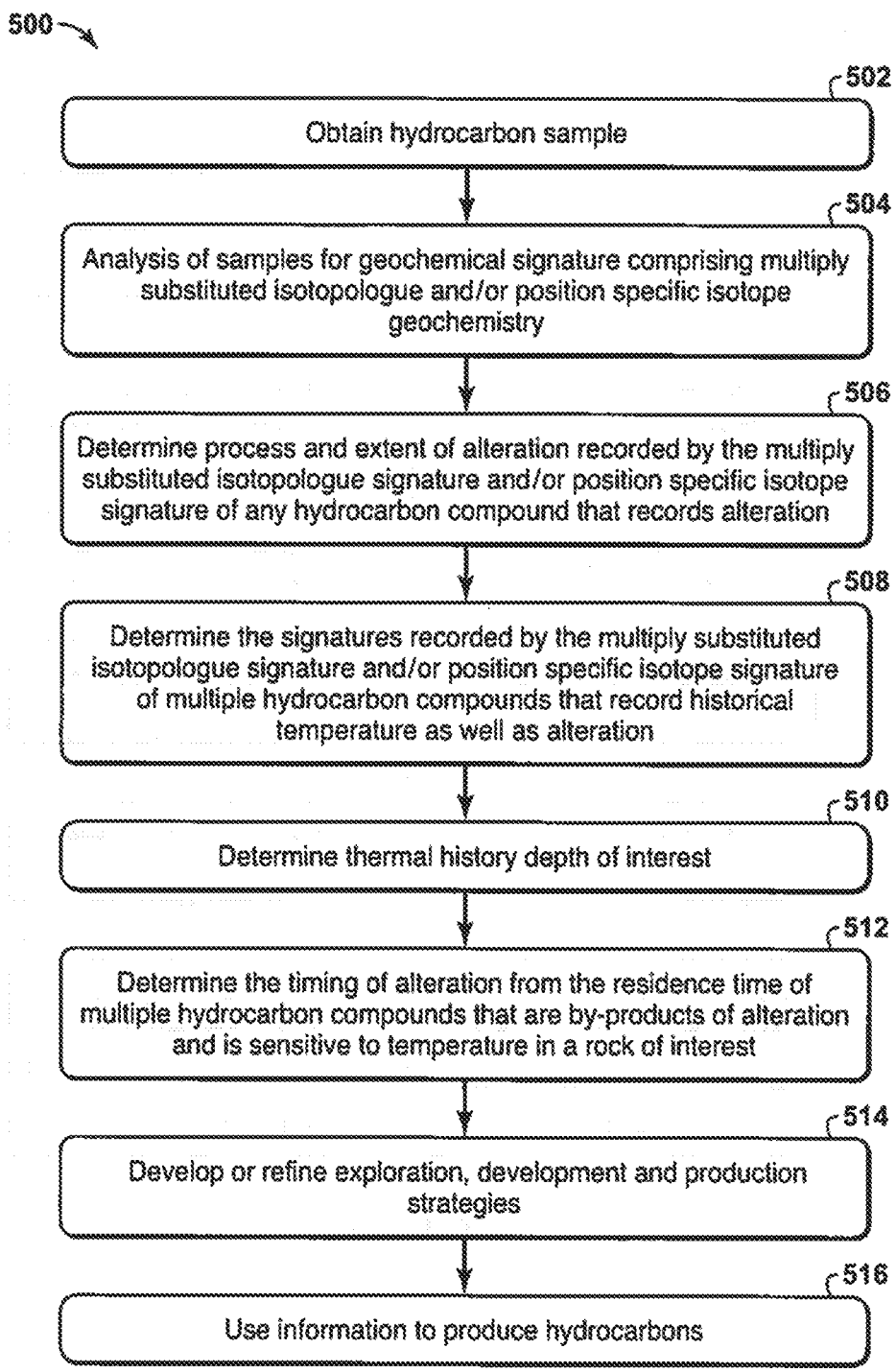
FIG. 5 is a flow diagram of an exemplary method to determine the extent and timing of alteration of hydrocarbons in accordance with an exemplary embodiment of the present techniques.

FIG. 5 is a flow diagram 500 of an exemplary method to determine the extent and timing of alteration of hydrocarbons to develop enhanced exploration, development and production strategies to discover and produce higher qualities of hydrocarbons in accordance with an exemplary embodiment of the present techniques. In this diagram 500, the extent and timing of alteration of hydrocarbon compounds is determined by comparing signatures provided by hydrocarbons that are sensitive to temperature and alteration. The signature that is sensitive to alteration provides an assessment of how extensive biodegradation has been on the compound. The temperature is used to determine when biodegradation occurred through integration with a time-temperature history provided by a basin model. Once an estimate of the extent of biodegradation and timing of biodegradation is known, one can use this information to identify structures that may be present at the time of hydrocarbon charge that did not have conditions favorable for biodegradation that may host hydrocarbons present day that are of greater quality and value.

The method begins in block 502. At block 502, a sample of hydrocarbons is obtained. Then, at block 504, the sample is analyzed for multiply substituted isotopologue signature and/or position specific isotope geochemical signatures. This obtaining the hydrocarbon sample may be similar to the discussion of block 202 of FIG. 2 and block 302 of FIG. 3, while the analysis of the samples may be similar to the discussion of block 204 of FIG. 2 and block 304 of FIG. 3.

At block 506, the process responsible for alteration recorded by the multiply substituted isotopologue signature and/or isotope position specific isotope signature in different hydrocarbon compounds is determined and the extent of alteration quantified. The process controlling the multiply substituted isotopologue or position specific isotope signature can be determined through molecular modeling approaches, through experimentation or empirical observations.

For example, one approach is to use molecular modeling techniques that predict the impact of multiply substituted isotopologue signatures as a function of increasing alteration for any given process. If one considers biodegradation, as an example, a molecular model can determine the impact of variable levels of biodegradation when molecules are likely to be impacted by biodegradation are known. For example, methane is not thought to be altered by biodegradation other than by receiving methane, as a by-product of the process. In contrast, propane is known to be a compound that can be altered by biodegradation. A model can therefore be developed to show the impact of any given alteration process (in this example biodegradation) on particular isotopologues of the hydrocarbon compound of interest (e.g., propane), or on particular position specific effects in the hydrocarbon compound.

Another example may be to experimentally determine the impact of a process on a hydrocarbon compound of interest in the laboratory. Using biodegradation again as an example, a hydrocarbon compound (e.g., propane) may be exposed to micro-organisms known to degrade the compound for different periods of time to produce propane that has experienced different levels of biodegradation. This propane may then be analyzed for its multiply substituted isotopologue signature and/or position specific isotope signatures to develop a model for how propane signatures evolve as a function of any given process.

Another example may be to compare the multiply substituted isotopologue signature and/or position specific isotope signature to data from empirical observations of other data sets for the same compound when the process controlling its signature is well known. For example, the multiply substituted isotopologue signature and/or position specific isotope signature of propane may be compared from the sample taken in block 502 with databases of samples previously analyzed from different locations that have experienced different alteration processes and at different levels of alteration. Once the signatures from block 502 are shown to match a process from the database, the database can be used to define a model for determining the extent of that process. Then, the signature measured in block 504 may be converted to a parameter and quantified indices. For example, if the process is controlling the signature is biodegradation, the measured signature is converted to some indices of biodegradation and a quantification of the level of biodegradation (e.g. 80% completion of biodegradation of propane).

In block 508, signatures recorded by the multiply substituted isotopologue signature and/or position specific isotope signature of multiple hydrocarbon compounds that record historical temperature as well as alteration are determined. This determination may include processing a series of signatures that are determined for compounds that are sensitive to the process of alteration determined in block 506 that also behave as temperature dependent compounds. For example, propane may be sensitive to biodegradation in a particular position (for example, the terminal carbon position) which enhances its use as an indicator of alteration. However, the multiply substituted isotopologue signature of the same molecule (but a different measurement or in a different position) may also be sensitive to temperature. Similarly, a position in butane and pentane may be sensitive to biodegradation, while a different position on the same compound may be sensitive to temperature.

In block 510, the thermal history of depth of interest may be determined. The determination may include the use of basin models or other techniques. For example, a time-temperature history for the rock hosting the altered hydrocarbon of interest may be determined in a variety of approaches. These models are typically calibrated with direct temperature information (e.g., from fluid inclusion temperatures) or indirect maturity information (e.g., vitrinite, molecular geochemistry etc.), thicknesses and lithologies for depth intervals in the subsurface, some estimation of paleo-water depth, and basal heat flow estimates.

In block 512, the timing of alteration from the residence time of multiple hydrocarbon compounds that are by-products of alteration and is sensitive to temperature in a rock of interest may be determined. For example, the alteration time of compounds measured in blocks 506 and block 508 are used to determine the timing of alteration. This may be performed as in block 410 of FIG. 4 using multiple approaches. One approach may be to use a statistical approach that considers the signatures of two compounds that are sensitive to alteration as determined and quantified in block 506 with different kinetic properties that record the same temperature in block 508 and at least two compounds with different kinetic properties that record independently different temperatures alongside the time-temperature history developed in block 510. From this, it is possible to calculate an absolute residence time (e.g., time since which the hydrocarbons have been altered) from the different multiply substituted isotopologue or position specific isotope signatures and the kinetic properties of different compounds by considering the impact of the time-temperature history of the rock in which these hydrocarbons were stored and altered. The residence time determined from block 512 above represents the time at which hydrocarbons were altered in the rock in which they are stored.

In block 514, exploration, development and production strategies may be developed or refined. For example, the information obtained in block 512 may be used to develop or refine an exploration, development and production strategy. In particular, the information about when hydrocarbons are altered in accumulations may be used to enhance target structures on a local or regional scale that may have conditions that do not support the particular alteration identified in block 506. For example, if hydrocarbons in one structure were shown to have undergone biodegradation it may be possible to find other prospects and structures that were located at greater depths (and hence temperatures) that do not allow biodegradation to occur. Such a method may enhance the ranking of prospects and ultimately improve exploration, development and production success by finding higher quality hydrocarbons.

These strategies may then be used to produce hydrocarbons from subsurface accumulations in block 516. The use of the strategies may be similar to the discussion of block 414 of FIG. 4.

Figure 6:
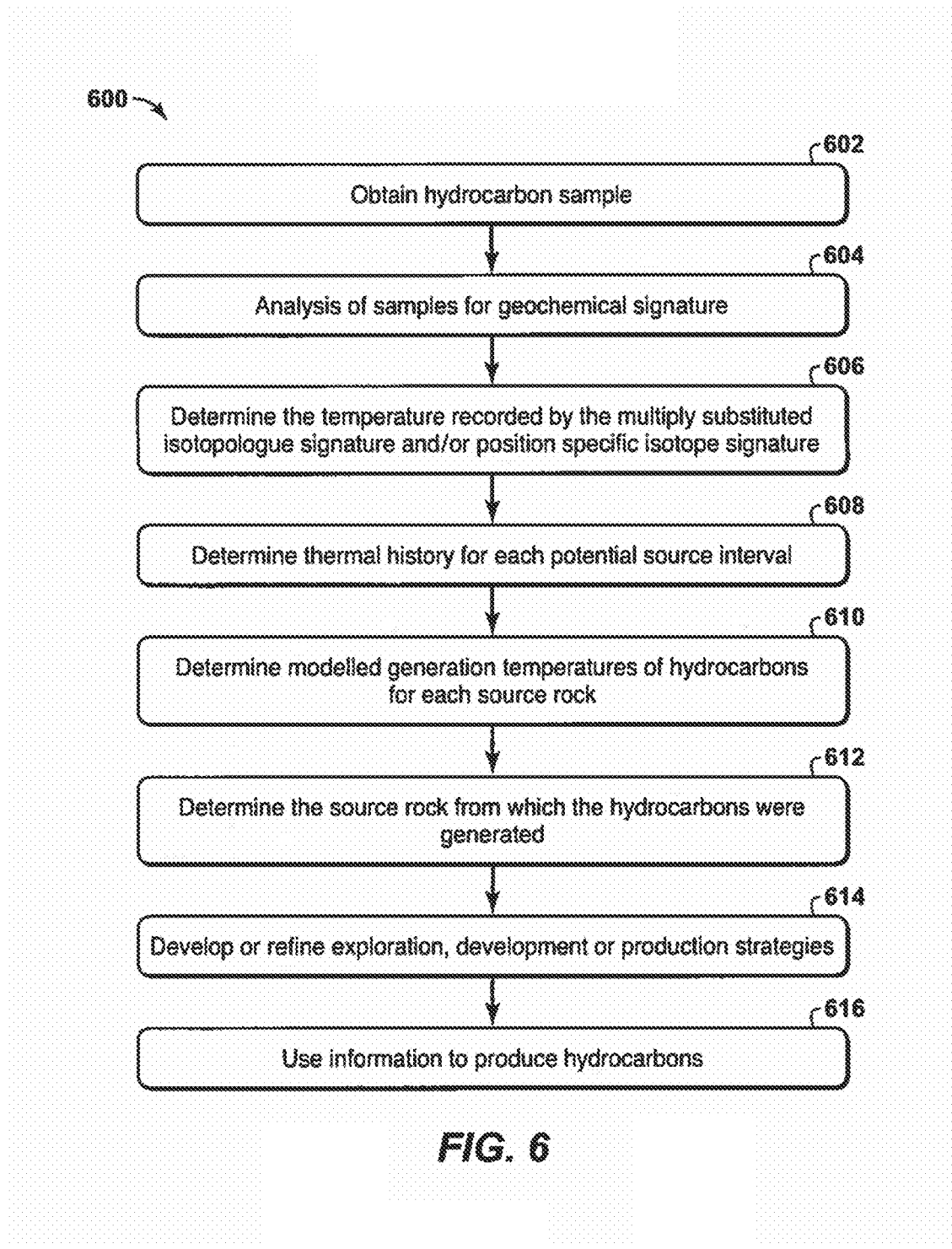
FIG. 6 is a flow diagram of an exemplary method to determine the source of hydrocarbon fluids when multiple sources are present in the subsurface in accordance with an exemplary embodiment of the present techniques.

FIG. 6 is yet another example of how multiply substituted isotopologue signature and position specific isotope signature may be used to improve prospect evaluation for subsequent ranking and improved exploration, development and production success. FIG. 6 is a flow diagram of an exemplary method to determine the source of hydrocarbon fluids when multiple sources are present in the subsurface in accordance with an exemplary embodiment of the present techniques. In this diagram 600, information on the presence and maturities of different source intervals provides confirmation of components within a hydrocarbon system that is used to develop exploration, development and production strategies to discover and produce higher quantities and qualities of hydrocarbons. For example, if the multiply substituted isotopologue or position specific isotope signature gives a temperature consistent with an inferred depth of one source rock, this may confirm its presence, if previously unknown, and also provide information on the maturity of the source rock. The particular type and maturity of the source rock has implications for whether the source is or has produced oil and/or gas or both. Alternatively, if multiple source rocks are present, this method provides a mechanism for the determination of the source(s) that generated the hydrocarbons. Once this information is known, where the sample was taken from to other parts of the basin may be extrapolated from the position in the basin using some knowledge of whether this source is deeper or shallower elsewhere to make predictions for source maturity and exploration potential.

The method begins in block 602. At block 602, a sample of hydrocarbons is obtained. Then, at block 604, the sample is analyzed for multiply substituted isotopologue signature and/or position specific isotope geochemical signatures. This obtaining the hydrocarbon sample may be similar to the discussion of block 202 of FIG. 2 and block 302 of FIG. 3, while the analysis of the samples may be similar to the discussion of block 204 of FIG. 2 and block 304 of FIG. 3.

Then, at block 606, the temperature recorded by the multiply substituted isotopologue signature and/or position specific isotope signature may be determined. For example, the temperature recorded by the multiply substituted isotopologue signature and/or isotope position specific isotope signature is determined for a given hydrocarbon compound that is sensitive to generation and does not equilibrate over geological timescales.

In block 608, a thermal history for each potential source interval is determined. The thermal history (or time-temperature history) may be determined for each potential source rock interval in the hydrocarbon system. This may be performed in a variety of methods, which may include basin modeling. These models are typically calibrated with direct temperature information (e.g., from fluid inclusion temperatures) or indirect maturity information (e.g., vitrinite, molecular geochemistry etc.), thicknesses and lithologies for depth intervals in the subsurface, some estimation of paleowater depth, and basal heat flow estimates.

In block 610, a modeled gas generation temperature is determined for each source rock. This determination, which may be performed for each source rock present in the hydrocarbon system, can be performed by taking the thermal history determined in block 608 and calculating the average gas generation temperature of the hydrocarbons produced. The volume of hydrocarbons generated may be modeled as a function of time and temperature using maturation and yield models, such as Burnham and Sweeney model and/or Burnham model. See, e.g., Burnham and Sweeney, "A chemical kinetic model of vitrinite maturation and reflectance", Geochimica et Cosmochimica Acta, Vol. 53, pp. 2649-2657 (1989) and Burnham, A simple kinetic model of petroleum formation and cracking, Lawrence Livermore National Laboratory report (1989). A modeled average gas generation temperature can be determined by calculating the volume of hydrocarbons generated at each time-temperature interval as a function of the time-temperature history. From this, the average temperature of hydrocarbon generation can be calculated by summing the product of the temperature and the volume produced at that temperature and dividing by the total volume of hydrocarbons generated.

In block 612, the source rock from which the hydrocarbons were generated may be determined. This determination may be performed by comparing the measured multiply substituted isotopologue signature of a hydrocarbon compound that records and preserved generation temperature (e.g., methane) in block 606 with the modeled generation temperatures for hydrocarbons generated from the different source rocks determined in block 610.

In block 614, exploration, development or production strategies may be developed or refined. For example, the information obtained in block 612 may be used to develop or refine an exploration, development and production strategy. In particular, the information may be used to determine what sources are producing hydrocarbons that are ultimately being stored to more effectively explore for hydrocarbons locally and regionally. As one example, if gases present in a structure originate from an over-mature, oil-prone source rock, then the exploration may involve or target oil in locations where this source is present, but at shallower depths where oil is the main product of hydrocarbon generation from the source rock. Such information may be useful for optimal evaluation of other prospects on a local or regional scale to enhance subsequent ranking of prospects and ultimately improve exploration, development and production success by finding larger volumes of and/or higher quality hydrocarbons.

These strategies may then be used to produce hydrocarbons from subsurface accumulations in block 616. The use of the strategies may be similar to the discussion of block 414 of FIG. 4.

Figure 7:
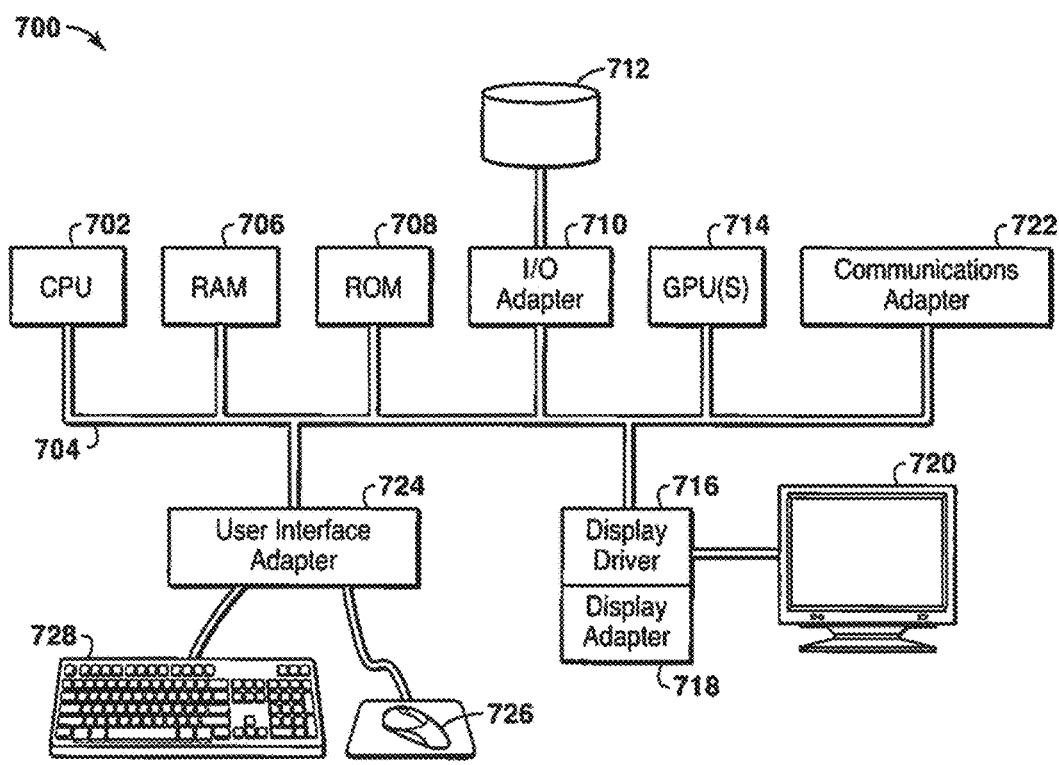
FIG. 7 is a block diagram of a computer system in accordance with an exemplary embodiment of the present techniques.

FIG. 7 is a block diagram of a computer system 700 in accordance with an exemplary embodiment of the present techniques. A central processing unit (CPU) 702 is coupled to system bus 704. The CPU 702 may be any general-purpose CPU, although other types of architectures of CPU 702 (or other components of exemplary system 700) may be used as long as CPU 702 (and other components of system 700) supports the inventive operations as described herein.

The CPU 702 may execute the various logical instructions according to various exemplary embodiments. For example, the CPU 702 may execute machine-level instructions for performing processing according to the operational flow described above.

The computer system 700 may also include computer components such as a random access memory (RAM) 706, which may be SRAM, DRAM, SDRAM, or the like. The computer system 700 may also include read-only memory (ROM) 708, which may be PROM, EPROM, EEPROM, or the like. RAM 706 and ROM 708 hold user and system data and programs, as is known in the art. The computer system 700 may also include an input/output (I/O) adapter 710, a communications adapter 722, a user interface adapter 724, and a display adapter 718. The I/O adapter 710, the user interface adapter 724, and/or communications adapter 722 may, in certain embodiments, enable a user to interact with computer system 700 in order to input information.

The I/O adapter 710 preferably connects a storage device (s) 712, such as one or more of hard drive, compact disc (CD) drive, floppy disk drive, tape drive, etc. to computer system 700. The storage device(s) may be used when RAM 706 is insufficient for the memory requirements associated with storing data for operations of embodiments of the present techniques. The data storage of the computer system 700 may be used for storing information and/or other data used or generated as disclosed herein. The communications adapter 722 may couple the computer system 700 to a network (not shown), which may enable information to be input to and/or output from system 700 via the network (for example, the Internet or other wide-area network, a local-area network, a public or private switched telephony network, a wireless network, any combination of the foregoing). User interface adapter 724 couples user input devices, such as a keyboard 728, a pointing device 726, and the like, to computer system 700. The display adapter 718 is driven by the CPU 702 to control, through a display driver 716, the display on a display device 720. Information and/or representations pertaining to a portion of a supply chain design or a shipping simulation, such as displaying data corresponding to a physical or financial property of interest, may thereby be displayed, according to certain exemplary embodiments.

The architecture of system 700 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

As an example, machine-readable logic or code may be used or executed with a computing system, such as computing system 700. The computer system may be used for exploration, production and development of hydrocarbons. The computer system may include a processor; memory in communication with the processor; and a set of instructions stored in memory and accessible by the processor. The set of instructions, when executed by the processor, are configured to: obtain information associated with a hydrocarbon sample; analyze the information for a geochemical signature, wherein the geochemical signature comprises one or more of a multiply substituted isotopologue signature and a position specific isotope signature; determine one or more of historical temperature, type of alteration, and extent of alteration from one or more of the multiply substituted isotopologue signature and position specific isotope signature; and develop or refining an exploration, development or production strategy based on the determined one or more of one or more of historical temperature, type of alteration, and extent of alteration.

Further, in other embodiments, the set of instructions may be configured to perform other operations. For example, the set of instructions may be configured to determine a main controlling process on the one or more of a multiply substituted isotopologue signature and a position specific isotope signature for at least one hydrocarbon compound; and convert the one or more of a multiply substituted isotopologue signature and a position specific isotope signature into a controlling parameter scale. Also, the set of instructions may be configured to present the converted one or more of the multiply substituted isotopologue signature and the position specific isotope signature; to determine a time-temperature history of a rock interval of interest; to assess impact of temperature on the one or more of the multiply substituted isotopologue signature and position specific isotope signature; and/or compare methane isotopes to a different hydrocarbon isotope to compare their different kinetic behaviors. In addition, the set of instructions may be configured to perform one or more of (i) molecular model equilibrium or non-equilibrium concentrations of multiply substituted isotopologues or positional effects to determine the one or more historical temperatures, type of alteration, and extent of alteration, and (ii) determine empirically by measurements of signatures of a given hydrocarbon compound at different temperatures to determine the one or more historical temperatures, type of alteration, and extent of alteration.

Still yet in other embodiments, the set of instructions may include other additional operations. For example, the set of instructions may be configured use a molecular model to predict the impact on the one or more of the multiply substituted isotopologue signature and position specific isotope signature as a function of increasing alteration for any given process. Also, the set of instructions may be configured to determine the historical temperature from the one or more of the multiply substituted isotopologue signature and position specific isotope signature; and develop a time-temperature history for a rock interval of interest; and/or to determine a measured temperature of a hydrocarbon compound with a known related kinetic property to determine one or more of corrected historical temperature, type of alteration, and extent of alteration for a hydrocarbon compound of interest. Also, the set of instructions may be configured to determine a thermal history of a depth of interest from a basin model and/or one or more of the multiply substituted isotopologue signature and position specific isotope signature; determine a timing of hydrocarbon charge from a residence time of a hydrocarbon in the rock of interest; and wherein the timing of the hydrocarbon charge is utilized in the development or refinement of an exploration, development or production strategy. The set of instructions may be configured to determine one or more of historical temperature, type of alteration, and extent of alteration for each of a plurality of hydrocarbon compounds from one or more of the multiply substituted isotopologue signature and position specific isotope signature associated with each of the plurality of hydrocarbon compounds. Further still, the set of instructions may be configured to perform basin modeling to correct the one or more of the multiply substituted isotopologue signature and position specific isotope signature and using the corrected one or more of the multiply substituted isotopologue signature and position specific isotope signature for the determining the thermal history of the depth of interest. Also, the set of instructions may be configured to determine a thermal history for each of a plurality of potential source and/or reservoir intervals from basin modeling; model generation temperatures for each of the plurality of potential source intervals; correct one or more of the multiply substituted isotopologue signature and position specific isotope signatures for kinetic related changes associated with the thermal history; determine the potential source interval for the one or more of the multiply substituted isotopologue signature and position specific isotope signature and the modelled generation temperatures; and wherein the determined potential source interval is utilized to develop or refine the exploration, development or production strategy.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

What is claimed is:

1. A method for exploration, production, and development of hydrocarbons comprising:
   obtaining a sample comprising hydrocarbons;
   analyzing the sample for a geochemical signature, wherein the geochemical signature comprises one or more of a multiply substituted isotopologue signature and a position specific isotope signature;
   determining one or more of type of alteration and extent of alteration, wherein the determining comprises comparing one or more of the multiply substituted isotopologue signature and position specific isotope signature of isotopes of different species of hydrocarbon compounds; and
   developing or refining an exploration, development, or production strategy based on the determined one or more of one of type of alteration and extent of alteration.

2. The method of claim 1, wherein determining one or more of type of alteration and extent of alteration comprises:
   determining a main controlling process on the one or more of a multiply substituted isotopologue signature and a position specific isotope signature for at least one hydrocarbon compound; and
   converting the one or more of a multiply substituted isotopologue signature and a position specific isotope signature into a controlling parameter scale.

3. The method of claim 2, further comprising presenting the converted one or more of the multiply substituted isotopologue signature and the position specific isotope signature.

4. The method of claim 2, further comprising determining a time-temperature history of a rock interval of interest.

5. The method of claim 1, wherein determining one or more of type of alteration and extent of alteration comprises assessing impact of time and temperature on the one or more of the multiply substituted isotopologue signature and position specific isotope signature.

6. The method of claim 1, wherein determining one or more of type of alteration and extent of alteration comprises one or more of (i) performing molecular modeling of equilibrium or non-equilibrium concentrations of multiply substituted isotopologues or positional effects to determine the one or more type of alteration and extent of alteration and (ii) determining empirically by measurements of signatures of a given hydrocarbon compound at different temperatures or that have undergone different processes and extents of alteration to determine the one or more type of alteration and extent of alteration.

7. The method of claim 1, wherein determining one or more of type of alteration and extent of alteration comprises comparing methane isotopes to a different hydrocarbon isotope to compare their different kinetic behaviors.

8. The method of claim 1, wherein determining one or more of type of alteration and extent of alteration comprises using a molecular model to predict the impact on the one or more of the multiply substituted isotopologue signature and position specific isotope signature as a function of increasing alteration for any given process.

9. The method of claim 1, wherein determining one or more of type of alteration and extent of alteration comprises:
   determining a historical temperature from the one or more of the multiply substituted isotopologue signature and position specific isotope signature; and
   developing a time-temperature history for a rock interval of interest.

10. The method of claim 9, further comprising determining a measured temperature of a hydrocarbon compound with a known related kinetic property to determine one or more of corrected type of alteration and extent of alteration for a hydrocarbon compound of interest.

11. The method of claim 1, further comprising:
    determining a thermal history of a depth of interest from one or more of the multiply substituted isotopologue signature and position specific isotope signature;
    determining a timing of hydrocarbon charge from a residence time of a hydrocarbon in the rock of interest; and
    wherein the timing of the hydrocarbon charge is utilized in the developing or refining an exploration, development, or production strategy.

12. The method of claim 11, further comprising determining one or more of type of alteration and extent of alteration for each of a plurality of hydrocarbon compounds from one or more of the multiply substituted isotopologue signature and position specific isotope signature associated with each of the plurality of hydrocarbon compounds.

13. The method of claim 11, wherein the determining one or more of type of alteration and extent of alteration comprises using the thermal history of the depth of interest from basin modeling to determine a residence time of hydrocarbons from the comparison of one or more of the multiply substituted isotopologue signature and position specific isotope signatures of one or more hydrocarbons when considering hydrocarbon compound specific kinetic property related changes to the multiply substituted isotopologue signatures and position specific isotope signatures.

14. The method of claim 1, further comprising:
    determining a thermal history for each of a plurality of potential source intervals and/or reservoir intervals from basin modeling;
    modeling generation temperatures for each of the plurality of potential source intervals;
    correcting one or more of the multiply substituted isotopologue signature and position specific isotope signatures for kinetic related changes associated with the thermal history;

determining the potential source interval from the one or more of the multiply substituted isotopologue signature and position specific isotope signature and the modeled generation temperature; and wherein the determined potential source interval is utilized in developing or refining the exploration, development, or production strategy.

15. A computer system for exploration, production, and development of hydrocarbons comprising:
a processor;
memory in communication with the processor; and
a set of instructions stored in memory and accessible by the processor, the set of instructions, when executed by the processor, are configured to:
obtain information associated with a hydrocarbon sample;
analyze the information for a geochemical signature, wherein the geochemical signature comprises one or more of a multiply substituted isotopologue signature and a position specific isotope signature;
determine one or more of type of alteration and extent of alteration, wherein the determining comprises comparing one or more of the multiply substituted isotopologue signature and position specific isotope signature of isotopes of different species of hydrocarbon compounds; and
develop or refine an exploration, development, or production strategy based on the determined one or more of type of alteration and extent of alteration.

16. The computer system of claim 15, wherein the set of instructions to determine one or more of type of alteration and extent of alteration are further configured to:
determine a main controlling process on the one or more of a multiply substituted isotopologue signature and a position specific isotope signature for at least one hydrocarbon compound; and
convert the one or more of a multiply substituted isotopologue signature and a position specific isotope signature into a controlling parameter scale.

17. The computer system of claim 16, further comprising a set of instructions to present the converted one or more of the multiply substituted isotopologue signature and the position specific isotope signature.

18. The computer system of claim 16, further comprising a set of instructions configured to determine a time-temperature history of a rock interval of interest.

19. The computer system of claim 15, wherein the set of instructions configured to determine one or more of type of alteration and extent of alteration further comprise a set of instructions configured to assess impact of temperature on the one or more of the multiply substituted isotopologue signature and position specific isotope signature.

20. The computer system of claim 15, wherein the set of instructions configured to determine one or more of type of alteration and extent of alteration further comprise a set of instructions configured to perform one or more of (i) performing molecular modeling of equilibrium or non-equilibrium concentrations of multiply substituted isotopologues or positional effects to determine the one or more type of alteration and extent of alteration, and (ii) determine empirically by measurement by measurements of signatures of a given hydrocarbon compound at different temperatures to determine the one or more type of alteration and extent of alteration.

21. The computer system of claim 15, wherein the set of instructions configured to determine one or more of type of alteration and extent of alteration further comprise a set of instructions configured to compare methane isotopes to a different hydrocarbon isotope to compare their different kinetic behaviors.

22. The computer system of claim 15, wherein the set of instructions configured to determine one or more of type of alteration and extent of alteration further comprise a set of instructions configured to use a molecular model to predict the impact on the one or more of the multiply substituted isotopologue signature and position specific isotope signature as a function of increasing alteration for any given process.

23. The computer system of claim 15, wherein the set of instructions are configured to determine one or more of type of alteration and extent of alteration further comprise a set of instructions configured to:
determine a historical temperature from the one or more of the multiply substituted isotopologue signature and position specific isotope signature; and
develop a time-temperature history for a rock interval of interest.

24. The computer system of claim 23, further comprising set of instructions configured to determine a measured temperature of a hydrocarbon compound with a known related kinetic property to determine one or more of corrected type of alteration and extent of alteration for a hydrocarbon compound of interest.

25. The computer system of claim 15, further comprising as set of instructions configured to:
determining a thermal history of a depth of interest from a basin model and/or one or more of the multiply substituted isotopologue signature and position specific isotope signature;
determining a timing of hydrocarbon charge from a residence time of a hydrocarbon in the rock of interest; and
wherein the timing of the hydrocarbon charge is utilized in the developing or refining an exploration, development, or production strategy.

26. The computer system of claim 25, further comprising a set of instructions configured to determine one or more of type of alteration and extent of alteration for each of a plurality of hydrocarbon compounds from one or more of the multiply substituted isotopologue signature and position specific isotope signature associated with each of the plurality of hydrocarbon compounds.

27. The computer system of claim 25, wherein the set of instructions configured to determine one or more of type of alteration and extent of alteration further comprises a set of instructions configured to use the thermal history of the depth of interest from basin modeling to determine a residence time of hydrocarbons from the comparison of the one or more of the multiply substituted isotopologue signature and position specific isotope signatures of one or more hydrocarbons when analyzing hydrocarbon compound specific kinetic property related changes to the multiply substituted isotopologue signatures and position specific isotope signatures.

28. The computer system of claim 15, further comprising a set of instructions configured to:
determine a thermal history for each of a plurality of potential source intervals and/or reservoir intervals from basin modeling;
model generation temperatures for each of the plurality of potential source intervals;
correct one or more of the multiply substituted isotopologue signature and position specific isotope signatures for kinetic related changes associated with the thermal history;

determine the potential source interval for the one or more of the multiply substituted isotopologue signature and position specific isotope signature and the modeled generation temperatures; and wherein the determined potential source interval is utilized to develop or refine the exploration, development, or production strategy.

* * * * *